(12) United States Patent
Muller et al.

(10) Patent No.: US 7,816,525 B1
(45) Date of Patent: Oct. 19, 2010

(54) PROCESS FOR THE PREPARATION OF OPTICALLY PURE TETRAHYDROPTERINS AND DERIVATIVES, AND SPECIFICALLY OF OPTICALLY PURE TETRAHYDROFOLIC ACID AND DERIVATIVES THEREOF, BY STEREOSPECIFIC HYDROGENATION

(75) Inventors: Hans Rudolf Muller, Schaffhausen (CH); Rudolf Moser, Schaffhausen (CH); Viola Groehn, Neuhausen am Rheinfall (CH); Benoit Pugin, Munchenstein (CH)

(73) Assignee: Merck & Cie, Schaffhausen (CH)

( * ) Notice: Subject to any disclaimer, the term of this patent is extended or adjusted under 35 U.S.C. 154(b) by 0 days.

(21) Appl. No.: 10/030,692

(22) PCT Filed: Jul. 12, 2000

(86) PCT No.: PCT/EP00/06646

§ 371 (c)(1), (2), (4) Date: Jan. 14, 2002

(87) PCT Pub. No.: WO01/04120

PCT Pub. Date: Jan. 18, 2001

(30) Foreign Application Priority Data

Jul. 14, 1999 (CH) .................................. 1301/99

(51) Int. Cl.
*C07D 475/04* (2006.01)
(52) U.S. Cl. ........................... 544/258; 544/261; 556/21
(58) Field of Classification Search ................. 544/267, 544/264, 269, 270, 271
See application file for complete search history.

(56) References Cited

U.S. PATENT DOCUMENTS

| | | | | |
|---|---|---|---|---|
| 4,133,831 A * | 1/1979 | Masaki et al. | ................ | 562/847 |
| 4,739,110 A * | 4/1988 | Drent | ......................... | 560/207 |
| 5,028,734 A * | 7/1991 | Drent | ......................... | 560/207 |
| 5,869,738 A * | 2/1999 | Pan et al. | ..................... | 560/207 |
| 6,162,914 A * | 12/2000 | Toderi et al. | ................ | 544/258 |
| 6,683,206 B2 * | 1/2004 | Stutz et al. | ................... | 562/465 |
| 6,858,731 B1 * | 2/2005 | Muller et al. | ................ | 544/258 |
| 2007/0197589 A1* | 8/2007 | Watson et al. | ................ | 514/315 |
| 2008/0306263 A1* | 12/2008 | Muller et al. | ................ | 544/258 |
| 2009/0036713 A1* | 2/2009 | Almena et al. | ............... | 564/214 |

FOREIGN PATENT DOCUMENTS

| EP | 0537842 | 4/1993 |
|---|---|---|
| EP | 0548895 | 6/1993 |
| EP | 0551642 | 7/1993 |
| EP | 0600460 | 6/1994 |
| EP | 0682026 | 11/1995 |
| EP | 0773221 | 5/1997 |

OTHER PUBLICATIONS

Boyle, JCS Chem. Comm 1974, pp. 375-376.*
IUPAC Compendium of Chemical Techinology 2nd Edition (1997), entry for phosphines, phosphoranes.*
Phosphine. ( 2007). In Britannica Concise Encyclopedia. Retrieved Jun. 22, 2007, from Encyclopædia Britannica Online: <http://www.britannica.com/ebc/article-9059776>.*
"Phosphine From Wikipedia, the free encyclopedia" <http://en.wikipedia.org/wiki/Phosphine> Downloaded from the internet Jun. 25, 2007.*
"Index by Molecular Formula" <http://lb.chemie.uni-hamburg.de/static/data/51_tc02t8rk.html> Downloaded from the internet Jun. 22, 2007.*
"Diphosphane (CHEBI:35880)" Downloaded from the internet Jun. 22, 2007 <http://www.ebi.ac.uk/chebi/searchld.do?chebild=CHEBI:35880>.*
Liddle, S.T. and Izod, K. Organometallics, 23, 23, 5550-5559, 2004.*
Andrews et al., Chem. Commun., 2000, 1961-1962.*
Warrener, Pure & App!. Chem., vol. 58, No. 1, pp. 161 and 164, 1986.*
"Acyl" Hawley's Condensed Chemical Dictionary, 14th Edition Copyright © 2002 downloaded from the internet Mar. 23, 2010.*
"Acyl" Dorland's Medical Dictionary downloaded from the internet Mar. 23, 2010.*
"Acyl From Wikipedia, the free encyclopedia" downloaded from the internet Mar. 23, 2010.*
Hackh's Chemical Dictionary (American and British usage) Revised and edited by Julius Grant. Third Edition. The Blakiston Company, Philadelphia, 1944, p. 18.*
McGraw-Hill Dictionary of Science and Technical Terms (McGraw-Hill, 1976) p. 22.*

* cited by examiner

*Primary Examiner*—Mark L Berch
(74) *Attorney, Agent, or Firm*—Millen, White, Zelano & Branigan, P.C.

(57) ABSTRACT

Process for the preparation of tetrahydropterin and tetrahydropterin derivatives by hydrogenating pterin and pterin derivatives with hydrogen in the presence of a hydrogenating catalyst, in which the hydrogenation is carried out in a polar reaction medium and metal complexes that are soluble in the reaction medium are employed as the hydrogenation catalysts. The process is suited to the hydrogenation, particularly asymmetric hydrogenation, of folic acid, folic acid salts, folic acid esters, folic acid ester salts or dihydroforms thereof, with the proviso that in the event of using folic acid, carboxylic acid salts thereof or dihydroforms thereof the reaction medium is aqueous, and in the event of using folic acid esters, folic acid ester salts or dihydroforms thereof the reaction medium is an alcohol. The process opens up straightforward access to achiral and chiral pterin derivatives.

22 Claims, No Drawings

PROCESS FOR THE PREPARATION OF OPTICALLY PURE TETRAHYDROPTERINS AND DERIVATIVES, AND SPECIFICALLY OF OPTICALLY PURE TETRAHYDROFOLIC ACID AND DERIVATIVES THEREOF, BY STEREOSPECIFIC HYDROGENATION

The present invention relates to a process for the preparation of tetrahydropterin and derivatives, especially tetrahydrofolic acid, tetrahydrofolic acid salts, tetrahydrofolic acid esters and salts of tetrahydrofolic acid esters, by hydrogenation of pterin or pterin derivatives, especially folic acid or folic acid salts, or of folic acid esters or salts of folic acid esters, in a polar reaction medium with dissolved metal complexes as the hydrogenation catalysts. The invention also relates to addition salts of folic acid esters and of tetrahydrofolic acid esters.

Pterin satisfies the formula

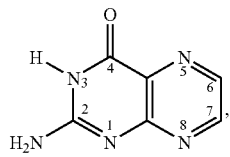

and it is known that derivatives of this bi-heterocyclic compound occur in nature and both natural and synthetic derivatives possess physiological efficacy, the action often being developed by 5,6,7,8-tetrahydropterins. The prospect of opening up access to tetrahydropterin and tetrahydropterin derivatives as intermediates or physiologically active compounds is therefore an attractive one. One known physiologically active tetrahydropterin derivative ist tetrahydrofolic acid, which inter alia as a leucocyte growth factor affects the formation of blood. Tetrahydrofolic acid is derived from folic acid.

Folic acid satisfies formula I,

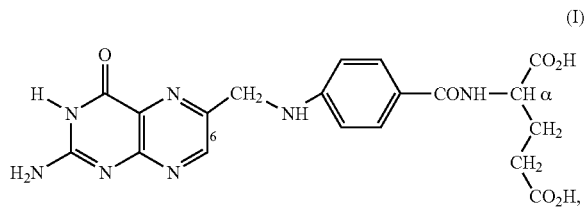

where the asymmetric αC atom may be present in the glutaminic acid radical in the S configuration (αS) or in the R configuration (αR). Hereinafter the enantiomers of folic acid will be referred to as (αS) folic acid and (αR) folic acid. The same goes for the folic acid esters and their derivatives. They will be referred to as (αS) folic acid esters and (αR) folic acid esters. Naturally occurring folic acid corresponds to (αS) folic acid.

Tetrahydrofolic acid satisfies formula II,

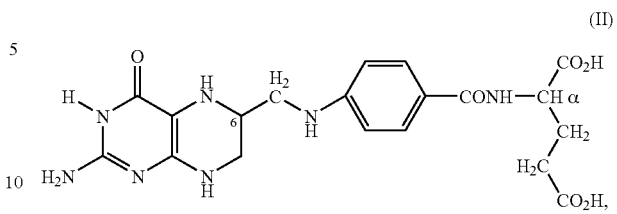

where the asymmetric αC atom may be present in the glutaminic acid radical in the S configuration (αS) or in the R configuration (αR) and the asymmetric C atom 6 may be present in the tetrahydropterin radical in the R configuration (6R) or S configuration (6S). The diastereomers of tetrahydrofolic acid will hereinafter be referred to as (6S,αS), (6S,αR), (6R,αS) and (6R,αR) tetrahydrofolic acid. The same goes for the tetrahydrofolic acid esters and their derivatives. They will be referred to as (6S,αS), (6S,αR), (6R,αS) and (6R,αR) tetrahydrofolic acid esters. Naturally occurring tetrahydrofolic acid corresponds to (6S,αS) tetrahydrofolic acid.

Hereinafter the term folic acid, folic acid esters and folic acid ester salts, unless designated otherwise, always embraces the two enantiomers (αS) and (αR) and the term tetrahydrofolic acid, tetrahydrofolic acid esters and tetrahydrofolic acid ester salts embraces all possible diastereomers. Within the framework of the invention the term folic acid ester salts and tetrahydrofolic acid ester salts embraces addition salts of folic acid esters and of tetrahydrofolic acid esters with acids.

Tetrahydrofolic acid has found broad therapeutic application in the form of 5-formyl or 5-methyl derivatives and their physiologically compatible salts. It has long been known that the biological activity of the naturally occurring diastereomers of the reduced folates and of those that do not occur in nature, for example of the natural (6S,αS) diastereomer of tetrahydrofolic acid and of the unnatural (6R,αS) diastereomer of tetrahydrofolic acid, are very different. Therefore it makes sense to provide therapeutic preparations that contain only the most active form or in which the latter is at least highly concentrated.

On an industrial scale tetrahydrofolic acid is generally made by heterogeneous hydrogenation of the two imino groups in the pterin system of (αS) folic acid, usually obtaining an equimolar mixture of two diastereomers, i.e. of (6S,αS) tetrahydrofolic acid and (6R,αS) tetrahydrofolic acid. The equimolar mixture can be used for pharmaceutical formulations. Beforehand, however, it is also possible to concentrate the desired diastereomer of tetrahydrofolic acid by fractionated crystallisation or to recover it in pure form, for which various processes are known; for example see EP-0 495 204. This process is not a serious contender from the economic viewpoint because from the start it means that the unwanted diastereomer will have to be used elsewhere.

In order to mitigate or even avoid this substance loss altogether, diastereoselective (asymmetric) hydrogenations of folic acid have also already been proposed. For instance, EP-0 551 642 describes how Rh(I) complexes immobilised on a carrier with optically active diphosphines are used to hydrogenate folic acid in an aqueous buffer solution. The optical yields achieved can be as high as around 50% de, though it must be remembered that these values may be falsified by derivatisation prior to determining the optical yield and need not match the actual values following hydrogenation. Indeed, even the inventor casts doubt on the values indicated in EP-0 551 642 (see H. Brunner et al. in Chem. Ber./Receuil, 1997, No. 130, pp. 55-61, specifically p. 56, right-hand column, 1$^{st}$ section). One drawback of this heterogeneous hydrogenation is the severely fluctuating diastereoselectivity which is due to the influence of the carrier material, and which considerably affects the reproducibility of the process. Moreover, it is necessary to employ low ratios of substrate to catalyst (large amounts of catalyst), because given a substrate/catalyst ratio of >40 both the chemical yield and the optical yield fall drastically. The separation, purification and re-use of the catalyst likewise leads to a deterioration in chemical and optical yield. A particular drawback is the low catalytic activity, which means that relatively long reaction times are required in spite of high catalyst concentrations. The process is therefore not suitable for industrial-scale production.

It is known from EP-0 256 982, EP-0 564 406 and EP-0 646 590 that iridium metal complexes can be used with chiral diphosphine ligands for the stereoselective hydrogenation of prochiral imines. However, the hydrogenation of imino groups that form part of an aromatic ring system is not disclosed.

P. H. Boyle et al. describe in Tetrahedron vol. 44, No. 16 (1988), pp. 5179-5188 how in the hydrogenation of folic acid silyl esters with an asymmetric rhodium/diphosphine complex in benzolic solution no hydrogen uptake whatsoever takes place even in the presence of water and the substrate is recovered unaltered.

Hydrogenations of pterin and pterin derivatives, such as for example folic acid, with hydrogen in a reaction medium and hydrogenation catalysts dissolved therein in the form of metal complexes are not yet known, although there is a technical need for such a process.

Surprisingly, it has been found that the imino groups in the aromatic pterin system, notably of folic acid and folic acid esters, can be hydrogenated with hydrogen in the presence of dissolved metal complexes as hydrogenation catalysts if polar reaction media are used, for example an aqueous or an alcoholic reaction medium. The process is characterised by surprisingly short reaction times with increased conversion rates, pointing to high catalytic activity and productivity which are observed even when increased ratios of substance to catalyst are used. The process is economical and reproducible and is also suited to industrial-scale implementation.

Surprisingly also, it was found that under these reaction conditions even asymmetric hydrogenations can be carried out and yet high optical yields achieved, which can exceed 50% ee or de, if metal complexes with chiral ligands are used as hydrogenation catalysts. For example, using an asymmetric hydrogenation it is possible to obtain from (αS) folic acid or (αS) folic acid esters, or (αS) folic acid ester salts, according to the optical induction of the ligand, mixtures of diastereomers in which respectively the (6R,αS) or (6S,αS) diastereomer predominates. If the starting compound is (αR) folic acid or (αR) folic acid esters, or (αR) folic acid ester salts, mixtures are obtained in which respectively the (6R,αR) or (6S,αR) diastereomer predominates.

A first subject-matter of the invention is a process for the preparation of tetrahydropterin and tetrahydropterin derivatives by the hydrogenation of pterin and pterin derivatives with hydrogen in the presence of a hydrogenation catalyst which is characterised by the fact that the hydrogenation is carried out in a polar reaction medium and metal complexes soluble in the reaction medium are used as the hydrogenation catalysts.

The hydrogenation can proceed via dihydropterin intermediate stages. The use of such intermediate stages, or rather of dihydropterins and dihydropterin derivatives as starting compounds for the hydrogenation, is also included within the framework of the invention. These starting compounds may be any of the tautomers, for example 5,6-, 7,8- and 5,8-dihydropterins and dihydropterin derivatives, as well as enamines (6-aminoethenyl tetrahydropterins and their derivatives).

Within the framework of the invention, polar reaction medium preferably means an aqueous or alcoholic reaction medium.

A preferred subject-matter of the invention is a process for the preparation of tetrahydrofolic acid, tetrahydrofolic acid salts, tetrahydrofolic acid esters or tetrahydrofolic acid ester salts by hydrogenation of folic acid, folic acid salts, folic acid esters or folic acid ester salts with hydrogen in the presence of a hydrogenation catalyst, said process being characterised by the fact that the hydrogenation is carried out at elevated pressure in the presence of metal complexes dissolved in the reaction medium as the hydrogenation catalysts, with the proviso that the reaction medium is aqueous where folic acid and carboxylic acid salts thereof are used, and that the reaction medium is alcoholic where folic acid esters and folic acid ester salts are used.

A further preferred subject-matter of the invention is a process for the preparation of chiral tetrahydropterin derivatives by the asymmetric hydrogenation of prochiral pterin derivatives with hydrogen in the presence of a hydrogenation catalyst, said process being characterised by the fact that the hydrogenation is carried out in a polar reaction medium and metal complexes that are soluble in the reaction medium are used as the hydrogenation catalysts, the metal complexes containing chiral ligands. Prochiral pterin derivatives for asymmetric hydrogenation are pterins substituted chiefly in 6-position, 7-position, or in 6- and 7-position.

Another preferred subject-matter of the invention is a process for the preparation of chiral tetrahydrofolic acid, chiral tetrahydrofolic acid salts, tetrahydrofolic acid esters or tetrahydrofolic acid ester salts by asymmetric hydrogenation of folic acid, folic acid salts, folic acid esters or folic acid ester salts with hydrogen in the presence of a hydrogenation catalyst, said process being characterised by the fact that the hydrogenation is carried out at elevated pressure in the presence of metal complexes dissolved in the reaction medium as the hydrogenation catalysts, the metal complexes containing chiral ligands, with the proviso that the reaction medium is aqueous where folic acid and carboxylic acid salts thereof are used, and that the reaction medium is alcoholic where folic acid esters and folic acid ester salts are used.

If (αS) or (αR) folic acid or carboxylic acid salts thereof, folic acid esters or folic acid ester salts are employed as the starting product for the hydrogenation, depending on the optical induction by the ligand in the metal complex the reaction products will contain a surplus of the (6S,αS) or (6R,αS), or (6S,αR) or (6R,αR) diastereomers, respectively. If an equimolar mixture of the (αS) and (αR) folic acid or carboxylic acid salts thereof, folic acid esters and folic acid ester salts is employed, depending on the optical induction by the ligand in the metal complex the reaction products will contain a surplus of either the (6R,αS), (6R,αR) or the (6S,αS), (6S, αR) diastereomers.

Within the framework of the invention, optical surplus in the case of asymmetric hydrogenation means that one diastereomer or a pair of diastereomers predominates in the mixture of the diastereomers. The ratio of one diastereomer or pair of diastereomers to the other is preferably not less than 55:45, more especially not less than 60:40, and most preferably not less than 75:25.

Pterin and prochiral pterins are known or can be produced using known or analogous processes. Prochiral pterins are substituted in either the 6-position or 7-position, or in the 6-position and 7-position. Prochiral pterins may satisfy formula A,

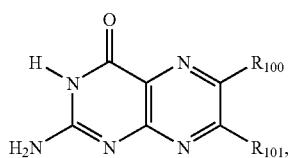

in which $R_{101}$ is H or independently has the meaning of $R_{100}$, and $R_{100}$ represents an organic radical attached via a C, O or N atom and having 1 to 50 carbon atoms, which is not interrupted or which is interrupted by one or more groups selected from —O—, —NH—, —N($C_1$-$C_4$-alkyl)-, —C(O)—, —C(O)O—, —OX(O)—, —OC(O)O—, —C(O)NH—, —NHC(O)—, —NHC(O)O—, —OC(O)NH—, —NHC(O)NH—, —C(O)N($C_1$-$C_4$-alkyl)-, —N($C_1$-$C_4$-alkyl)C(O)—, —N($C_1$-$C_4$-alkyl)C(O)O—, —OC(O)N($C_1$-$C_4$-alkyl)-, —N($C_1$-$C_4$-alkyl)C(O)N($C_1$-$C_4$-alkyl)-, and which is unsubstituted or is substituted with F, Cl, Br, —CN, —OCN, —NCO, —OH, —$NH_2$, —NH$C_1$-$C_4$-alkyl, —N($C_1$-$C_4$-alkyl)$_2$, $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, —C(O)OH, —C(O)O$M_{100}$, —C(O)O$C_1$-$C_4$-alkyl, —C(O)$NH_2$, —C(O)NH$C_1$-$C_4$-alkyl, —C(O)N($C_1$-$C_4$-alkyl)$_2$, $R_{102}$—C(O)O—, $R_{102}$—OC(O)O—, $R_{102}$-C(O)NH—, $R_{102}$—C(O)N($C_1$-$C_4$-alkyl)-, $R_{102}$—NHC(O)NH—, $R_{103}$C(O)— or —CH(O), $M_{100}$ stands for Li, K, Na, $NH_4^+$, or ammonium with 1 to 16 carbon atoms, $R_{102}$ stands for $C_1$-$C_6$-alkyl, $C_5$- or $C_6$-cycloalkyl, phenyl or benzyl, and $R_{103}$ denotes $C_1$-$C_4$-alkyl, phenyl or benzyl.

As organic radical, $R_{100}$ contains preferably 1 to 30 carbon atoms, more preferably 1 to 20 carbon atoms, and most preferably 1 to 12 carbon atoms, and if appropriate at least 1 heteroatom selected from the group comprising O, N and P. Examples of organic radicals are alkyl, cycloalkyl, cycloalkylalkyl, phenyl, naphthyl, pnenylalkyl and naphthylalkyl, as well as corresponding heteroradicals with heteroatoms selected from the group comprising O and N.

The $C_1$-$C_4$ alkyl group preferably denotes methyl or ethyl. $R_{101}$ preferably stands for H. $M_{100}$ as ammonium with 1 to 16 carbon atoms may for example be $H_3N(C_1N(C_1$-$C_4$-alkyl)$^+$, $H_2N(C_1$-$C_4$-alkyl)$_2^+$, $HN(C_1$-$C_4$-alkyl)$_3^+$ or $N(C_1$-$C_4$-alkyl)$_4^+$; with alkyl preferably being methyl, ethyl or n-butyl. As the alkyl, $R_{102}$ preferably contains 1 to 4 carbon atoms and may for example be methyl, ethyl, propyl and butyl. $R_{103}$ preferably denotes methyl, ethyl or phenyl.

A preferred sub-group of formula A compounds are those in which $R_{101}$ stands for H and $R_{100}$ denotes —$CH_3$, phenyl, —CH=O, $C_2$-$C_6$-mono- or polyhydroxyalkyl (if appropriate substituted with acetyl, trifluoracetyl or =O), —C(O)—$C_1$-$C_4$-alkyl, —C(O)OH, C(O)O$C_1$-$C_4$-alkyl, —C(O)$NH_2$, —C(O)NH$C_1$-$C_4$-alkyl, —C(O)N($C_1$-$C_4$-alkyl)$_2$, —$CH_2$($CH_2$)$_{0.1}$—OH, —$CH_2$($CH_2$)$_{0.1}$—$NH_2$, —$CH_2$($CH_2$)$_{0.1}$—NH$C_1$-$C_4$-alkyl, or —CH($R_{104}$)—($R_{105}$)-p-$C_6H_4$—C(O)—$R_{106}$, $R_{104}$ represents H, methyl or ethyl, $R_{105}$ denotes a direct bond, —$CH_2$—, —O—, —NH—, —$NCH_3$—, —N[HC(O)]—, —N[$CH_3$C(O)]—, —N[$CF_3$C(O)]—, —NHC(O)—, or —OC(O)—, and $R_{106}$ stands for —OH, —$NH_2$, —$NHCH_3$, —N($CH_3$)$_2$, or —NH$R_{107}$, where $R_{107}$ is a radical, attached via an α-carbon atom, of a natural or unnatural amino acid or of a peptide from natural or unnatural amino acids having 2 to 12 amino acid units.

The monohydroxyalkyl or polyhydroxyalkyl contains preferably 2 to 4 carbon atoms and preferably 1 to 4OH groups attached to different carbon atoms.

Some examples of $R_{100}$ in formula A include —CHO, —C(O)—$CH_3$, —$CH_2$—$NH_2$, —$CH_2CH_2$—$NH_2$, —$CH_2$—OH, —$CH_2CH_2$—OH, —C(O)—OH, —$CH_2$—C(O)—OH, —C(O)—$NH_2$, —$CH_2$—C(O)—$NH_2$, —$CH_2$—NH-p-$C_6H_4$—C(O)OH (when $R_{101}$ equals H=pteroic acid), —$CH_2CH_2$—NH-p-$C_6H_4$—C(O)OH, —$CH_2CH_2$—NH-p-$C_6H_4$—C(O)—NH—CH($CO_2H$)—$CH_2CH_2$—C(O)OH (when $R_{101}$ equals H=homofolic acid), —C(O)—CH(OH)—$CH_3$, biopterins when $R_{101}$ equals H and $R_{100}$ equals —CH(OH)—CH(OH)—$CH_3$, and neopterins when $R_{101}$ equals H and $R_{100}$ equals —CH(OH)—CH(OH)—$CH_2$—OH, —$CH_2$—N(CHO)-p-$C_6H_4$—C(O)—NH—CH($CO_2H$)—$CH_2CH_2$—C(O)OH (when $R_{101}$ equals H=10-formylfolic acid), and —$CH_2$—NH-p-$C_6H_4$—C(O)—NH—CH($CO_2H$)—$CH_2CH_2$—C(O)OH (when $R_{101}$ equals H=folic acid). The chiral carbon atoms of the biopterins and neopterins may be in the form of racemates or optical isomers, for example

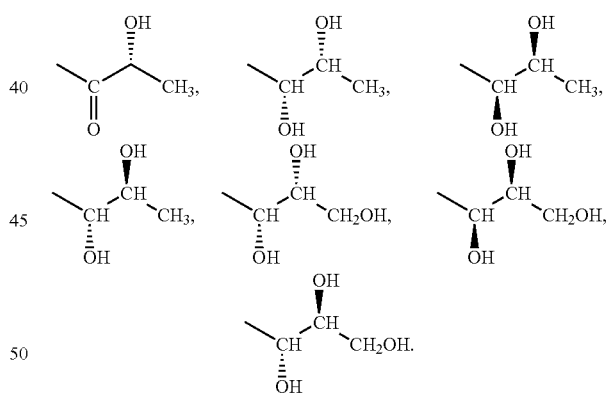

Metal complexes as soluble hydrogenation catalysts essentially contain d-8 metals; especially preferred being d-8 metals selected from the group comprising rhodium (Rh), iridium (Ir) and ruthenium (Ru).

Ligands for metals as soluble hydrogenation catalysts frequently contain tertiary amino and/or phosphine groups as complexing groups, the ligands forming a 5- to 10-membered, preferably 5- to 7-membered ring with the metal atom. Preferred are ligands that contain one tertiary amino group and one tertiary phosphine group or two tertiary phosphine groups.

Especially preferred are organic achiral or chiral ditertiary diphosphine ligands. Within the framework of the invention, the term chiral ditertiary diphosphine ligands means that the diphosphine has at least one chiral element and includes at least two optical isomers. The optical isomerism may for example be governed by stereogenic centres (asymmetric carbon atoms), atropic isomerism or planar chirality. Stereogenic centres may be present in the phosphine substituents and/or in the skeleton and/or side groups of the skeleton of the diphosphine. The optical induction can be controlled or reversed by the choice of enantiomers or diastereomers of ligands. If this cannot be forecast, the optical induction can be ascertained by a simple test. The hydrogenation of folic acid ester salts with the catalyst Rh/(R)-BINAP leads for example to the (6S,αS) diastereomer of the tetrahydrofolic acid dimethylester salt being concentrated. If the same hydrogenation is carried out with the catalyst Rh/(S)-BINAP, the result will be an equally high concentration of the (6R,αS) diastereomer of the tetrahydrofolic acid dimethylester salt.

Folic acid can be employed as pure (αS)- or (αR) folic acid or in any desired mixing ratio of the two enantiomers. Suitable folic acid esters can be obtained using standard esterification processes. The folic acid esters may contain the same hydrocarbon radicals or heterohydrocarbon radicals in the ester group as described hereinafter for the formula III compounds, including the preferences. (αS) folic acid and (αS) folic acid esters are preferred.

The folic acid may also be in the form of its carboxylic acid salts. Suitable examples include alkali metal and alkaline earth metal salts and ammonium salts. Of the alkali metal and alkaline earth metal salts, the sodium, potassium, magnesium and calcium salts are preferred. Of the ammonium salts, $NH_4^+$ and the cations of primary, secondary and tertiary amines and quaternary ammonium are suitable. The amines may for example have 1 to 30 carbon atoms, preferably 1 to 24 carbon atoms, and the quaternary ammonium may for example have 4 to 40, preferably 4 to 32 carbon atoms. Some examples of the ammonium are methyl, ethyl, n-propyl, n-butyl, n-hexyl, n-octyl, phenyl, benzyl, dimethyl, diethyl, di-n-propyl, di-n-butyl, di-n-hexyl, di-n-octyl, methyl-ethyl, methyl-n-butyl, methyl-n-octyl, tetramethylene or pentamethylene, trimethyl, triethyl, tri-n-butyl, tri-n-octyl, tetramethyl, tetra-n-butyl, tetra-n-octyl and trimethyl-n-octyl ammonium. The amino groups of the folic acid salts may additionally also form a salt with monobasic to tribasic inorganic or organic acids, and contain the group x HA, where x and HA have the meanings given hereinafter for folic acid ester salts of formula III, including the preferences.

The folic acid ester salts in the form of their enantiomers or mixtures thereof may satisfy formula III,

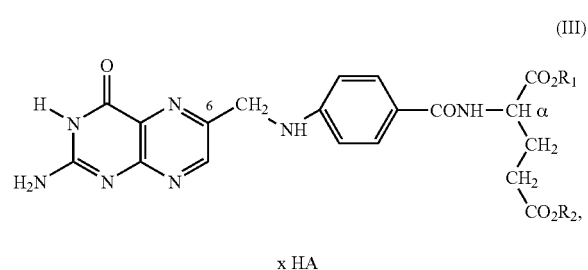

(III)

x HA in which $R_1$ or $R_2$ are H, and one of $R_1$ or $R_2$, or both $R_1$ and $R_2$ independently of one another represent a monovalent hydrocarbon radical or a heterocarbon radical attached via a carbon atom, with heteroatoms selected from the group —O—, —S— and —N—, HA stands for a monobasic to tribasic inorganic or organic acid and x denotes an integer from 1 to 6 or fractional number between 0 and 6.

$R_1$ and $R_2$ may be chosen independently of one another, but they are preferably identical. It is preferred if $R_1$ and $R_2$ represent a hydrocarbon radical. When $R_1$ and $R_2$ are hydrocarbon radicals they may be aliphatic radicals with 1 to 20, preferably 1 to 12, more preferably 1 to 8, and most preferably 1 to 4 carbon atoms; cycloaliphatic or cycloaliphatic-aliphatic radicals with 3 to 8 cyclic carbon atoms and 1 to 6 carbon atoms in the aliphatic radical; aromatic hydrocarbon radicals with 6 to 14 carbon atoms, more preferably 6 to 10 carbon atoms, or aromatic-aliphatic radicals with 7 to 15 carbon atoms, more preferably 7 to 10 carbon atoms.

The heterohydrocarbon radical may be heteroalkyl with 2 to 16 carbon atoms, preferably 2 to 10 carbon atoms, and most preferably 2 to 6 carbon atoms; heterocycloaliphatic radicals with 3 to 8, preferably 5 or 6 ring links; heterocycloaliphatic-aliphatic radicals with 3 to 8, preferably 5 or 6 ring links, and 1 to 6, preferably 1 to 4 carbon atoms in the aliphatic radical; heteroaromatic radicals with preferably 4 to 13 carbon atoms, most preferably 4 to 9 carbon atoms, and at least one heteroatom; and heteroaromatic-aliphatic radicals with preferably 4 to 13 carbon atoms, most preferably 4 to 9 carbon atoms, and at least one heteroatom, and 1 to 6, preferably 1 to 4 carbon atoms in the aliphatic radical; the heteroradicals contain at least one heteroatom selected from the group comprising —O—, —S— and —N— and preferably —O— and —N—.

The hydrocarbon radicals may for example be selected from the group comprising linear and branched $C_1$-$C_{20}$-alkyl, $C_3$-$C_8$-cycloalkyl and preferably $C_4$-$C_7$-cycloalkyl, $C_3$-$C_8$-cycloalkyl-$C_1$-$C_6$-alkyl and preferably $C_4$-$C_7$-cycloalkyl-$C_1$-$C_4$-alkyl, $C_8$-$C_{10}$-aryl or $C_7$-$C_{12}$-aralkyl.

The heterohydrocabon radicals may for example be selected from the group comprising $C_2$-$C_{16}$-heteroalkyl, $C_2$-$C_2$-heterocycloalkyl and preferably $C_4$-$C_5$-heterocycloalkyl, $C_4$-$C_7$-heterocycloalkyl-$C_1$-$C_6$-alkyl and preferably $C_4$-$C_5$-heterocycloalkyl-$C_1$-$C_6$-alkyl, $C_4$-$C_9$-heteroaryl and preferably $C_4$-$C_5$-heteroaryl, and $C_5$-$C_{12}$-heteroaralkyl and preferably $C_5$-$C_{10}$-heteroaralkyl; the heteroradicals contain 1 to 3 and preferably 1 or 2 heteroatoms from the group comprising —O— and —N—.

$R_1$ and $R_2$ may be linear or branched alkyl, which preferably contains 1 to 12, more preferably 1 to 8, and most preferably 1 to 4 carbon atoms. Examples include methyl, ethyl, and the isomers of propyl, butyl, pentyl, hexyl, heptyl, octyl, decyl, dodecyl, tetradecyl, hexadecyl, octadecyl and eicosyl. The alkyl is preferably linear and it is preferably methyl, ethyl, n-propyl and n-butyl.

As cycloalkyl, $R_1$ and $R_2$ contain preferably 4 to 7 and most preferably 5 or 6 cyclic carbon atoms. Examples of cycloalkyl include cyclopropyl, cyclobutyl, cyclopentyl, cyclohexyl, cycloheptyl and cyclooctyl. Most preferred is cyclohexyl.

As cycloalkyl alkyl, $R_1$ and $R_2$ contain preferably 4 to 7 and most preferably 5 or 6 cyclic carbon atoms, and preferably 1 to 4 and most preferably 1 or 2 carbon atoms in the aliphatic radical. Examples of cycloalkyl alkyl include cyclopropyl methyl or cyclopropyl ethyl, cyclobutyl methyl or cyclobutyl propyl, cyclopentyl methyl or cyclopentyl ethyl, cyclohexyl methyl or cyclohexyl ethyl, cycloheptyl methyl and cyclooctyl methyl. Most preferred is cyclohexyl methyl or cyclohexyl ethyl.

As aryl, $R_1$ and $R_2$ may stand for naphthyl and preferably phenyl. As aralkyl, $R_1$ and $R_2$ are preferably phenylalkyl with preferably 1 to 4 carbon atoms in the alkyl. Examples include benzyl and β-phenylethyl.

As heteroalkyl, $R_1$ and $R_2$ may for example be $C_1$-$C_4$-alkyl-$X_1$—$C_2$-$C_4$-alkyl, where $X_1$ stands for O or $NC_1$-$C_4$-alkyl. Examples include methoxy ethyl and ethoxy ethyl.

As heterocycloalkyl, $R_1$ and $R_2$ may for example be pyrrolidinyl, piperidinyl, morpholinyl, tetrahydropyranyl or piperazinyl.

As heterocycloalkyl alkyl, $R_1$ and $R_2$ may for example be pyrrolidinyl methyl or pyrrolidinyl ethyl, piperidinyl methyl or piperidinyl ethyl, morpholinyl methyl or morpholinyl ethyl, tetrahydropyranyl methyl or tetrahydropyranyl ethyl, or piperazinyl methyl or piperazinyl ethyl.

As heteroaryl, $R_1$ and $R_2$ may for example be thiophenyl, furanyl, pyranyl, pyrrolyl, imidazolyl, pyridinyl, pyrimidinyl, pyrazinyl, indolyl, quinolinyl, oxazolyl or isooxazolyl.

As heteroaralkyl, $R_1$ and $R_2$ may for example be furanyl methyl or furanyl ethyl, pyranyl methyl or pyranyl ethyl, pyrrolyl methyl or pyrrolyl ethyl, imidazolyl methyl or imidazolyl ethyl, pyridinyl methyl or pyridinyl ethyl, pyrimidinyl methyl or pyrimidinyl ethyl, pyrazinyl methyl or pyrazinyl ethyl, indolyl methyl or indolyl ethyl, quinolinyl methyl or quinolinyl ethyl.

One preferred group of formula III compounds are those in which $R_1$ and $R_2$ independently of one another represent $C_1$-$C_4$ alkyl, $C_5$-cycloalkyl or $C_6$-cycloalkyl, phenyl, $C_1$-$C_4$-alkyl phenyl, benzyl or $C_1$-$C_4$-alkyl benzyl. It is preferred if $R_1$ and $R_2$ are identical radicals. It is specifically preferred if $R_1$ and $R_2$ represent $C_1$-$C_4$ alkyl, for example methyl or ethyl.

In formula III, x preferably denotes an integer from 1 to 4 or a fractional number between 0.2 and 4, especially an integer from 1 to 3 or a fractional number between 0.5 and 3, and most preferably 1 or 2 or a fractional number between 0.5 and 2.

If the acid HA in formula III is derived from an inorganic acid, it may for example be HCl, HBr, $H_1$, $H_2SO_3$, $H_2SO_4$, $H_2CO_3$, $HNO_3$, $H_3PO_3$, $H_3PO_4$, $HBF_4$ or $H_2PF_6$.

HA in formula III preferably represents an organic acid. The organic acids are preferably derived from carboxylic acids, sulphonic acids, and phosphonic acids that contain 1 to 18, preferably 1 to 12, and most preferably 1 to 8 carbon atoms.

It is preferred if the organic acids satisfy formula IV, $$R_3—X_2—OH \qquad (IV),$$

in which $X_2$ stands for —C(O)—, —S(O)$_2$— or —P(O)OH—, and $R_3$ denotes linear or branched $C1$-$C_{18}$-alkyl, unsubstituted or substituted with a halogen, especially fluorine or chlorine, hydroxyl, carboxyl, nitrile, $C_1$-$C_4$ alkyl, $C_1$-$C_4$-alkoxy or $C_1$-$C_4$-haloalkyl, and preferably $C_1$-$C_{12}$-alkyl, $C_3$-$C_8$-cycloalkyl and preferably $C_4$-$C_7$-cycloalkyl, $C_3$-$C_8$-cycloalkyl-$C_1$-$C_4$-alkyl and preferably $C_4$-$C_7$-cycloalkyl-$C_1$-$C_4$-alkyl, $C_6$-$C_{10}$-aryl or $C_7$-$C_{12}$-aralkyl.

$R_3$ may be linear or branched alkyl which preferably and most preferably contains 1 to 4 carbon atoms. Examples include methyl, ethyl, and the isomers of propyl, butyl, pentyl, hexyl, heptyl, octyl, decyl, dodecyl, tetradecyl, hexadecyl, octadecyl and eicosyl. In preference the alkyl is linear and it is preferred if the alkyl is methyl, ethyl, n-propyl and n-butyl.

As cycloalkyl, $R_3$ contains preferably 4 to 7, most preferably 5 or 6 cyclic carbon atoms. Examples of cycloalkyl include cyclopropyl, cyclobutyl, cyclopentyl, cyclohexyl, cycloheptyl and cyclooctyl. Cyclohexyl is especially preferred.

As cycloalkyl alkyl, $R_3$ contains preferably 4 to 7, most preferably 5 or 6 cyclic carbon atoms, and preferably 1 to 4 and most preferably 1 or 2 carbon atoms in the aliphatic radical. Examples of cycloalkyl alkyl include cyclopropyl methyl or cyclopropyl ethyl, cyclobutyl methyl or cyclobutyl propyl, cyclopentyl methyl or cyclopentyl ethyl, cyclohexyl methyl or cyclohexyl ethyl, cycloheptyl methyl and cyclooctyl methyl. Cyclohexyl methyl or cyclohexyl ethyl is especially preferred.

As aryl, $R_3$ may stand for naphthyl and preferably phenyl. As aralkyl, $R_2$ is preferably phenyl alkyl with preferably 1 to 4 carbon atoms in the alkyl. Examples include benzyl and α-phenyl ethyl.

It is especially preferred if $X_2$ in formula IV stands for —S(O)$_2$—.

Some preferred examples of organic acids include acetic, propionic, butyric, mono-, di- and trichloroacetic acid, mono-, di- and trifluoroacetic acid, hydroxyacetic acid, oxalic acid, malonic acid, cyclohexane monodicarboxylic acid and cyclohexane dicarboxylic acid, benzoic acid, phthalic acid and terephthalic acid, trifluoromethyl benzoic acid, phenyl acetic acid, phenyl phosphonic acid, methyl sulphonic acid, ethyl sulphonic acid, propyl sulphonic acid, butyl sulphonic acid, cyclohexyl sulphonic acid, phenyl sulphonic acid, methyl phenyl sulphonic acid, trifluoromethyl phenyl sulphonic acid, mono-, di- and trichloromethyl sulphonic acid, and mono-, di- and trifluoromethyl sulphonic acid. Unsubstituted and substituted phenyl sulphonic acids are especially preferred.

The (αS) and (αR) enantiomers, respectively, of the folic acid esters may satisfy formula IIIa,

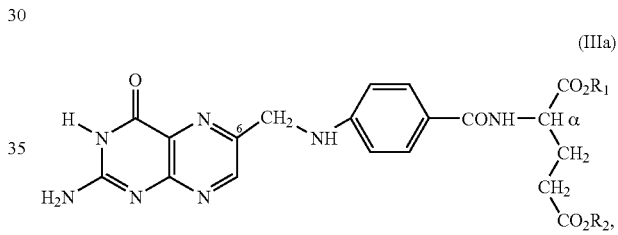

(IIIa)

in which $R_1$ and $R_2$ have the meanings given for the formula III compounds, including the preferences.

The folic acid or carboxylic acid salts thereof, folic acid esters and folic acid ester salts and enantiomers thereof may be partially or fully dissolved in the reaction medium. There will be a suspension or emulsion in the case of partial solution. It has proved expedient for folic acid or carboxylic acid salts thereof, folic acid esters and folic acid ester salts to be dissolved in the reaction medium to at least 0.5 g per liter of solvent, preferably to at least 1 g per liter, more preferably to at least 5 g per liter and most preferably to at least 10 g per liter.

The process may be carried out at a hydrogen pressure of 1 to 500 bars, preferably 1 to 150 bars, more preferably 1 to 120 bars, and most preferably 5 to 100 bars.

The reaction temperature may for example be 0 to 150° C., preferably 10 to 120° C. and most preferably 10 to 100° C.

The amount of catalyst is determined principally by the desired reaction time and by economic considerations. Larger amounts of catalyst essentially encourage shorter reaction times. The molar ratio of substrate to catalyst may for example be 10 to 100,000, preferably 20 to 20,000, more preferably 50 to 10,000, and specifically 100 to 5,000.

Within the framework of the invention, aqueous reaction medium means that only water or water in admixture with anorganic solvent is present. The proportion of water is preferably at least 30, more preferably at least 50 and specifically at least 70 percent by volume. It is most preferred of all if the reaction medium contains only water. Examples of suitable solvents include alcohols such as methanol, ethanol, propanol, butanol, ethylene glycol, and ethylene glycol monomethyl ether; ethers such as diethyl ether, diisobutyl ether, tetrahydrofuran and dioxan; sulphoxides and sulphones such as dimethyl sulphoxide, dimethyl sulphone, tetramethylene sulphone; and N-substituted carboxylic acid amides and lactams such as N-methylpyrrolidone and dimethylformamide. Two-phase hydrogenation is performed if solvents are not miscible with water.

Buffers, bases and/or acids can be added to the aqueous reaction medium. The reaction may for example be carried out at a pH from 1 to 10, preferably 3 to 9 and most preferably 5 to 8. Specific suitable buffers are phosphate buffers; however, carboxylic acids, carbonic acid, phosphoric acid and boric acid may also be used. Examples of suitable bases are alkali metal hydroxides and alkaline earth metal hydroxides, amines, and alkali metal salts of carboxylic acids, carbonic acid, phosphoric acid and boric acid. Examples of suitable acids include HCl, HBr, HI, $HBF_4$, $HClO_4$, carboxylic acids (if appropriate fluorinated or chlorinated acetic acid, benzoic acid, citric acid), boric acid, phosphoric acid, methane sulphonic acid, sulphuric acid and carbonic acid. The bases and acids may also be soluble or insoluble polymers such as, for example, ion exchangers. The amount of bases, acids and/or buffers may for example be 0 to 2, preferably 0 to 1, and specifically 0 to 0.5 mole per liter of water.

Within the framework of the invention, alcoholic reaction medium denotes the presence of an alcohol, by itself or in admixture with another organic solvent. Suitable alcohols include aliphatic, cycloaliphatic, cycloaliphatic-aliphatic and araliphatic alcohols. Some preferred examples are methanol, ethanol, n- or i-propanol, n-, i- or t-butanol, pentanol, hexanol, cyclohexanol, cyclohexanediol, hydroxymethyl cyclohexane or dihydroxymethyl cyclohexane, benzyl alcohol, ethylene glycol, diethylene glycol, propanediol, butanediol, ethylene glycol monomethyl ether or ethylene glycol monoethyl ether, and diethylene glycol monomethyl ether or diethylene glycol monoethyl ether. Preferred are methanol, ethanol, ethylene glycol, 1,2-propanediol and i-propanol. The alcoholic proportion is preferably at least 30, more preferably at least 50 and specifically at least 70 percent by volume. It is specifically preferred if only one alcohol is used. The stereoselectivity of the hydrogenation also depends on the reaction medium used. Two-phase hydrogenation is performed if a solvent is not miscible with alcohol.

Examples of suitable organic solvents include ethers such as diethyl ether, diisobutyl ether, tetrahydrofuran and dioxan; sulphoxides and sulphones such as dimethyl sulphoxide, dimethyl sulphone, tetramethylene sulphone; N-substituted carboxylic acid amides and lactams such as N-methylpyrrolidone and dimethyl formamide; ketones such as acetone or methyl-isobutyl ketone; and carboxylic acid esters such as methyl acetate, ethyl acetate, and methyl propionate.

Preferred catalyst metals are rhodium, iridium and ruthenium. The term catalysts also embraces catalyst precursors that are converted into catallytically active species before or during hydrogenation through contact with hydrogen.

It is known that the catalytic properties of the employed diphosphine catalysts can be influenced by the addition of metal halides and amonium halides. It may therefore be advantageous to add alkali metal chlorides or ammonium chlorides, ammonium bromides or ammonium iodides to the reaction mixture, for example LiCl, LiBr, LiI, NaI, NaBr or tetrabutyl ammonium iodide. The quantity may for example be 0.001 to 5 moles per liter of solvent. Other modifiers and co-catalysts may also be added, for example phthalimides, hydantoin or parabanic acid.

Examples of suitable ligands for metal complexes include tertiary phosphines, especially triarylphosphines, for example triphenyl phosphine, tritoluoyl phosphine and trixylyl phosphine, and tricycloalkyl phosphines, for example tricyclohexyl phosphine, and tertiary phosphanes, for example tetramethylene phenylphosphine or pentamethylene phenylphosphine. Especially suitable are bidentate ligands such as for example achiral or chiral ditertiary diphosphines, or tertiary phosphinoimines. Examples of the latter are

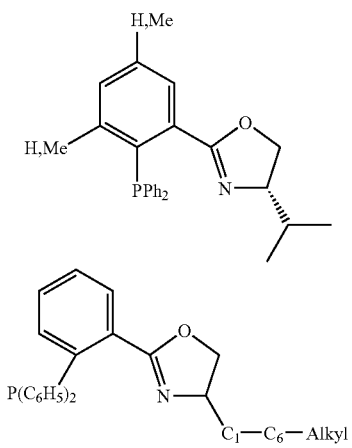

which are described by A. Lightfoot et al. in Angew. Chem. Int. Ed. 1998, 37, No. 20, pages 2897-2899 and P. Schnider et al., Chem. Eur. J., 1997, vol. 3, No. 6.

Large numbers of achiral ditertiary diphosphines and chiral ditertiary diphosphines for asymmetric hydrogenation catalysts in an alcoholic reaction medium are described in the literature; for example see H. Brunner and W. Zettlmeier, Handbook of Enantioselective Catalysis, vol. II: Ligand References, published by VCH Verlagsgesellschaft mbH, Weinheim (1993).

The achiral and chiral ditertiary diphosphines may also be ones in which the phosphine groups are attached (a) to various carbon atoms of a carbon chain having 2 to 4 carbon atoms, or (b) directly or via a bridging group —$CR_aR_b$— in the ortho positions of a cyclopentadienyl ring or to a respective cyclopentadienyl of a ferrocenyl, where $R_a$ and $R_b$ are the same or different and stand for H, $C_1$-$C_8$ alkyl, $C_1$-$C_4$ fluoroalkyl, $C_5$-$C_6$ cycloalkyl, phenyl, benzyl, or phenyl or benzyl substituted with 1 to 3 $C_1$-$C_4$ alkyl or $C_1$-$C_4$ alkoxy. $R_b$ stands preferably for hydrogen. $R_a$ preferably means $C_1$-$C_4$ alkyl.

The phosphine groups preferably contain two identical or different, preferably identical unsubstituted or substituted hydrocarbon radicals with 1 to 20, preferably 1 to 12 carbon atoms. Of the ditertiary diphosphines the ones that are especially preferred are those in which the two phosphine groups are two identical or different radicals selected from the group comprising linear or branched $C_1$-$C_{12}$ alkyl; $C_5$-$C_{12}$ cycloalkyl, $C_5$-$C_{12}$ cycloalkyl-$CH_2$—, phenyl or benzyl, unsubstituted or substituted with $C_1$-$C_6$ alkyl or $C_1$-$C_6$ alkoxy; or contain phenyl or benzyl substituted with halogen (for example F, Cl and Br), $C_1$-$C_6$ alkyl, $C_1$-$C_6$ haloalkyl (for example trifluoromethyl), $C_1$-$C_6$ alkoxy, $C_1$-$C_6$ haloalkoxy (for example trifluoromethoxy), $(C_6H_5)_3Si$, $(C_1$-$C_{12}$ alkyl$)_3$ Si, —$NH_2$, —$NH(C_1$-$C_2$) alkyl), —NH(phenyl), —NH(benzyl), —N(C$_1$-C$_{12}$ alkyl)$_2$, —N (phenyl)$_2$, N(benzyl)$_2$, morpholinyl, piperidinyl, pyrrolidinyl, piperazinyl, -ammonium-X$_3$—, —SO$_3$M$_1$, —PO$_3$M$_1$, or —CO$_2$—C$_1$-C$_6$ alkyl (for example —CO$_2$CH$_3$), where M$_1$ represents an alkali metal or hydrogen, and X$_3^-$ is the anion of a monobasic acid. M$_1$ preferably stands for H, Li, Na and K. X$_3^-$ represents the anion of a monobasic acid, preferably Cl$^-$, Br$^-$, or the anion of a monocarboxylic acid, for example formiate, acetate, trichloroacetate or trifluoroacetate.

The two radicals of the phosphine groups may respectively together also denote tetramethylene, pentamethylene or 3-oxa-pentane-1,5-diyl, unsubstituted or substituted with halogen, C$_1$-C$_6$ alkyl or C$_1$-C$_6$ alkoxy. The substituents are preferably attached to the P atom in the ortho positions.

The phosphine groups may also be ones of the formulas

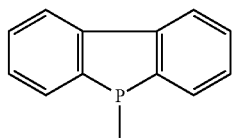 or 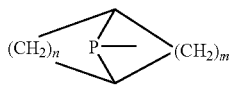

in which m and n independently of one another are an integer from 2 to 10, and the sum of m+n is 4 to 12 and preferably 5 to 8. Examples are [3.3.1]- and [4.2.1]-phobyl of the formulas

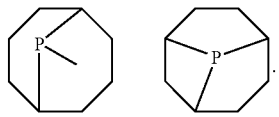

Examples of alkyl that preferably contains 1 to 6 carbon atoms are methyl, ethyl, n-propyl, i-propyl, n-butyl, i-butyl, t-butyl, and the isomers of pentyl and hexyl. Examples of cycloalkyl, if appropriate substituted with alkyl, are cyclopentyl, cyclohexyl, methyl cyclohexyl and ethyl cyclohexyl, and dimethyl cyclohexyl. Examples of phenyl and benzyl substituted with alkyl, alkoxy, haloalkyl and haloalkoxy are methyl phenyl, dimethyl phenyl, trimethyl phenyl, ethyl phenyl, methyl benzyl, methoxy phenyl, dimethoxy phenyl, trifluoromethyl phenyl, bis-trifluoromethyl phenyl, tris-trifluoromethyl phenyl, trifluoromethoxy phenyl and bis-trifluoromethoxy phenyl.

Preferred phosphine groups are ones containing identical or different, preferably identical radicals selected from the group comprising C$_1$-C$_6$-alkyl, cyclopentyl, either unsubstituted or substituted with 1 to 3 C$_1$-C$_4$-alkyl or C$_1$-C$_4$-alkoxy; benzyl and especially phenyl, unsubstituted or substituted with 1 to 3 C$_1$-C$_4$-alkyl, C$_1$-C$_4$-alkoxy, F, Cl, C$_1$-C$_4$-fluoroalkyl or C$_1$-C$_4$-fluoroalkoxy.

The diphosphines preferably satisfy formula IV, $$R_4R_5P—R_6—PR_7R_8 \quad (IV),$$

in which

R$_4$, R$_5$, R$_7$ and R$_3$ independently of one another represent a hydrocarbon radical with 1 to 20 carbon atoms which are unsubstituted or substituted with halogen, C$_1$-C$_6$-alkyl, C$_1$-C$_6$-haloalkyl, C$_1$-C$_6$-alkoxy, C$_1$-C$_6$-haloalkoxy, (C$_6$H$_5$)$_3$Si, (C$_1$-C$_{12}$-alkyl)$_3$Si, —NH$_2$, —NH(C$_1$-C$_{12}$-alkyl), —NH (phenyl), —NH(benzyl), —N(C$_1$-C$_{12}$-alkyl)$_2$, —N (phenyl)$_2$, —N(benzyl)$_2$, morpholinyl, piperidinyl, pyrrolidinyl, piperazinyl, -ammonium-X$_3$—, —SO$_3$M$_1$, —CO$_2$M$_1$, —PO$_3$M$_1$, or —CO$_2$—C$_1$-C$_6$-alkyl, where M$_1$ represents an alkali metal or hydrogen, and X$_3^-$ is the anion of a monobasic acid; or R$_4$ and R$_5$ and R$_7$ and R$_8$ respectively together denote tetramethylene, pentamethylene or 3-oxa-pentane-1,5-diyl, unsubstituted or substituted with halogen, C$_1$-C$_6$-alkyl or C$_1$-C$_6$-alkoxy, and R$_6$ is C$_2$-C$_4$-alkylene, unsubstituted or substituted with C$_1$-C$_6$-alkyl, C$_1$-C$_6$-alkoxy, C$_5$-cycloalkyl or C$_6$-cycloalkyl, phenyl, naphthyl or benzyl; 1,2- or 1,3-cycloalkylene, 1,2- or 1,3-cycloalkenylene, 1,2- or 1,3-bicycloalkylene or 1,2- or 1,3-bicycloalkenylene with 4 to 10 carbon atoms, unsubstituted or substituted with C$_1$-C$_6$-alkyl, phenyl or benzyl; 1,2- or 1,3-cycloalkylene, 1,2- or 1,3-cycloalkenylene, 1,2- or 1,3-bicycloalkylene or 1,2- or 1,3-bicycloalkenylene with 4 to 10 carbon atoms, unsubstituted or substituted with C$_1$-C$_6$-alkyl, phenyl or benzyl, and attached at whose 1- and/or 2-position(s) or at whose 3-position is methylene or C$_2$-C$_4$-alkylidene; 1,4-butylene, substituted in the 2,3-positions with R$_9$R$_{10}$C(O—)$_2$, and in the 1- and/or 4-positions unsubstituted or substituted with C$_1$-C$_6$-alkyl, phenyl or benzyl, and where R$_9$ and R$_{10}$ independently of one another represent hydrogen, C$_1$-C$_6$-alkyl, phenyl or benzyl; 3,4- or 2,4-pyrrolidinylene or methylene-4-pyrrolidine-4-yl, the N-Atom of which is substituted with hydrogen, C$_1$-C$_{12}$-alkyl, phenyl, benzyl, C$_1$-C$_{12}$-alkoxycarbonyl, C$_1$-C$_8$-acyl, C$_1$-C$_{12}$-alkylamino carbonyl; or 1,2-phenylene, 2-benzylene, 1,2-xylylene, 1,8-naphthylene, 2,2'-dinaphthylene or 2,2'-diphenylene, unsubstituted or substituted with halogen, —OH, C$_1$-C$_6$-alkyl, C$_1$-C$_6$-alkoxy, phenyl, benzyl, phenyloxy or benzyloxy; or R$_6$ stands for a radical of the formulas

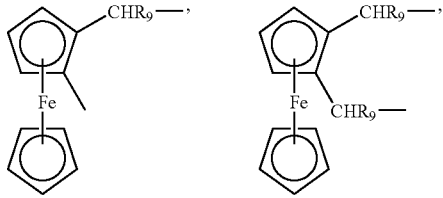

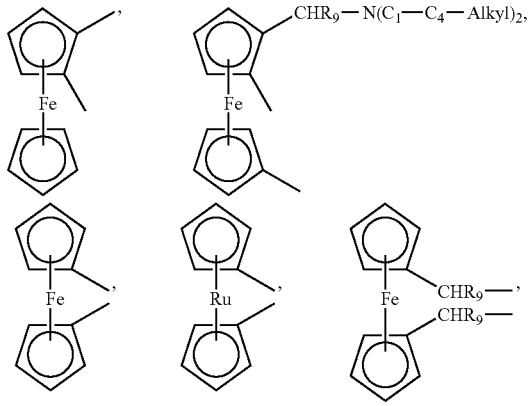

-continued

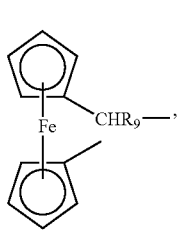 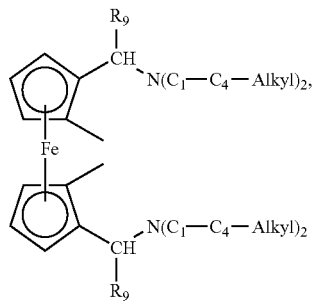

in which $R_9$ denotes hydrogen, $C_1$-$C_8$-alkyl, $C_1$-$C_4$-fluoroalkyl, unsubstituted phenyl or phenyl substituted with 1 to 3 F, Cl, Br, $C_1$-$C_4$-alkyl, $C_1$-$C_4$-alkoxy or fluoromethyl.

It is preferred if $R_4$, $R_5$, $R_7$ and $R_8$ are identical or different radicals, more especially identical radicals selected from the group comprising $C_1$-$C_6$-alkyl, unsubstituted cyclopentyl or cyclohexyl or cyclopentyl, or cyclohexyl substituted with one to three $C_1$-$C_4$-alkyl or $C_1$-$C_4$-alkoxy, unsubstituted benzyl or benzyl substituted with one to three $C_1$-$C_4$-alkyl or $C_1$-$C_4$-alkoxy, and especially phenyl, unsubstituted or substituted with one to three $C_1$-$C_4$-alkyl, $C_1$-$C_4$-alkoxy, —$NH_2$, OH, F, Cl, $C_1$-$C_4$-fluoroalkyl or $C_1$-$C_4$-fluoroalkoxy.

A preferred group of achiral and chiral diphosphines are those of formulas V to (XVII) and (XIX) to XXIII,

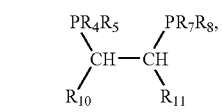 (V)

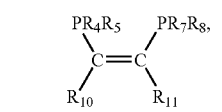 (VI)

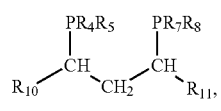 (VII)

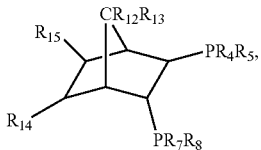 (VIII)

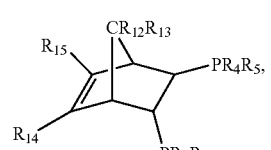 (IX)

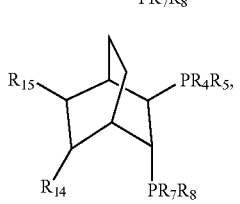 (X)

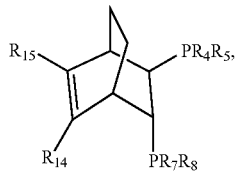 (XI)

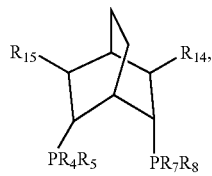 (XII)

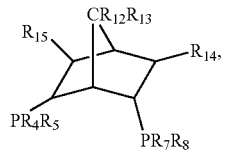 (XIII)

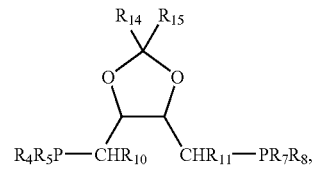 (IVX)

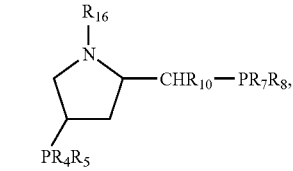 (XV)

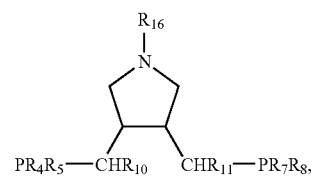 (XVI)

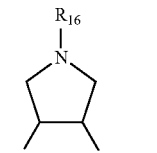 (XVII)

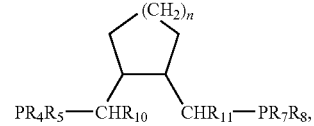 (XIX)

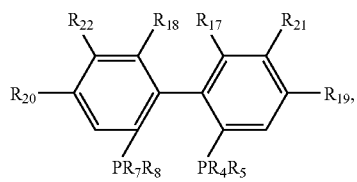 (XX)

-continued

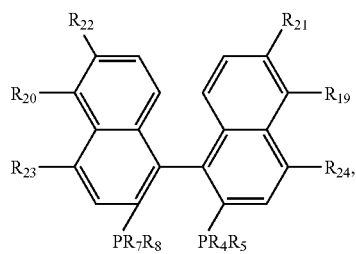
(XXI)

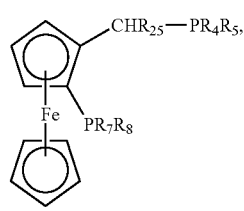
(XXII)

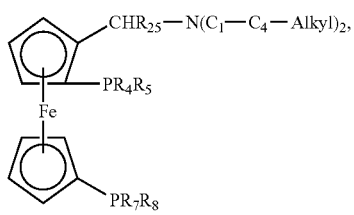
(XXIII)

in which $R_4$, $R_5$, $R_7$ and $R_8$ have the meanings stated earlier, including the preferences, $R_{10}$ and $R_{11}$ independently of one another denote hydrogen, $C_1$-$C_4$ alkyl or benzyl or phenyl, unsubstituted or substituted with one to three $C_1$-$C_4$ alkyl or $C_1$-$C_4$ alkoxy, $R_{12}$ and $R_{13}$ independently of one another represent hydrogen, $C_1$-$C_4$ alkyl, phenyl or benzyl, $R_{14}$ and $R_{15}$ independently of one another denote hydrogen, $C_1$-$C_4$ alkyl, $C_1$-$C_4$ alkoxy, or benzyl or phenyl, unsubstituted or substituted with one to three $C_1$-$C_4$ alkyl or $C_1$-$C_4$ alkoxy, $R_{16}$ represents hydrogen, $C_1$-$C_{12}$ alkyl, unsubstituted benzyl or phenyl, or benzyl or phenyl substituted with one to three $C_1$-$C_4$ alkyl or $C_1$-$C_4$ alkoxy, $C_1$-$C_{12}$ alkoxy-C(O)—, unsubstituted phenyl-C(O)— or benzyl-C(O)—, or phenyl-C(O)— or benzyl-C(O)— substituted with one to three $C_1$-$C_4$ alkyl or $C_1$-$C_4$ alkoxy, $C_1$-$C_{12}$ alkyl-NH—CO—, or phenyl-NH—C(O)— or benzyl-NH—C(O)—, unsubstituted or substituted with one to three $C_1$-$C_4$ alkyl or $C_1$-$C_4$ alkoxy, n stands for 0, 1 or 2, $R_{17}$ and $R_{18}$ are $C_1$-$C_4$ alkyl or $C_1$-$C_4$ alkoxy, or $R_{17}$ and $R_{18}$ together denote oxadimethylene, $R_{19}$, $R_{20}$, $R_{21}$, $R_{22}$, $R_{23}$ and $R_{24}$ are independently of one another H, $C_1$-$C_4$ alkyl, $C_1$-$C_4$ alkoxy, $C_5$- or $C_6$ cycloalkyl or $C_5$- or $C_6$ cycloalkoxy, phenyl, benzyl, phenoxy, benzyloxy, halogen, OH, —(CH$_2$)$_3$—C(O)—O—$C_1$-$C_4$ alkyl, —(CH$_2$)$_3$—C(O)—N($C_1$-$C_4$-alkyl)$_2$ or —N($C_1$-$C_4$-alkyl)$_2$, or $R_{19}$ and $R_{21}$, and/or $R_{17}$ and $R_{21}$, and/or $R_{20}$ and $R_{22}$, and/or $R_{18}$ and $R_{22}$, or $R_{21}$ and $R_{23}$ and/or $R_{22}$ and $R_{24}$ respectively together represent a fused-on 5 or 6-membered, monocyclic or bicyclic hydrocarbon ring, and $R_{25}$ is $C_1$-$C_4$ alkyl.

Some preferred examples of chiral ditertiary diphosphines are those of the following formulas V to XL:

(XXIV)

(XXV)

(XXVI)

(XXVII)

(XXVIII)

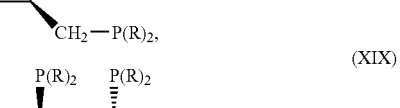
(XIX)

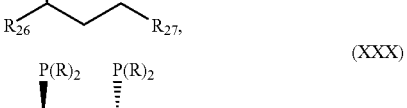
(XXX)

(XXXI)

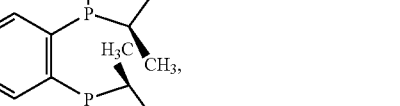
(XXXII)

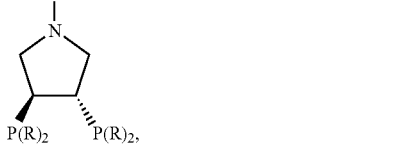
(XXXIII)

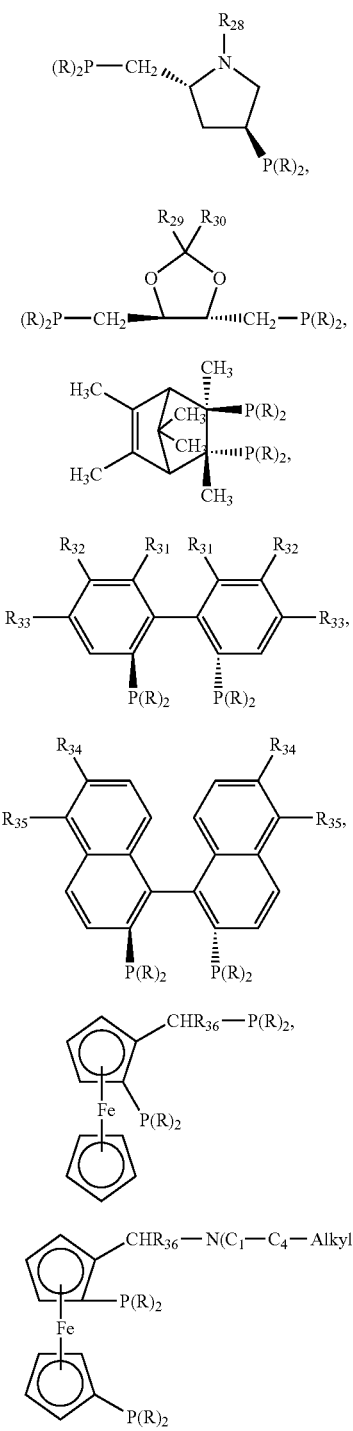

(XXXIV)

(XXXV)

(XXXVI)

(XXXVII)

(XXXVIII)

(XXXIX)

(XL)

in which

R stands for cyclohexyl or unsubstituted phenyl or phenyl substituted with one to three $C_1$-$C_4$-alkyl, $C_1$-$C_4$-alkoxy, trifluoromethyl, or an —$NH_2$ ($C_1$-$C_4$-alkyl)NH—, ($C_1$-$C_4$-alkyl)$_2$N—, $R_{26}$ and $R_{27}$ independently of one another denote $C_1$-$C_4$-alkyl, phenyl or benzyl and most preferably methyl, $R_{28}$ represents $C_1$-$C_8$-alkyl, $C_1$-$C_8$-acyl or $C_1$-$C_8$-alkoxycarbonyl, $R_{29}$ stands for hydrogen or independently has the meaning of $R_{30}$, and $R_{30}$ represents $C_1$-$C_4$-alkyl, phenyl or benzyl, $R_{31}$ denotes methyl, methoxy, or both $R_{31}$ together denote oxadimethylene, $R_{32}$ and $R_{33}$ independently of one another represent H, $C_1$-$C_4$-alkyl, $C_1$-$C_4$-alkoxy or ($C_1$-$C_4$-alkyl)$_2$N—, $R_{34}$ and $R_{35}$ independently of one another represent H, $C_1$-$C_4$-alkyl, $C_1$-$C_4$-alkoxy, —($CH_2$)$_3$—C(O)—O—$C_1$-$C_4$-alkyl, —($CH_2$)$_3$—C(O)—N($C_1$-$C_4$-alkyl)$_2$ or one pair $R_{34}$ and $R_{35}$ together represents a radical of formula XLI and the other pair $R_{34}$ and $R_{35}$ together represents a radical of formula XLII

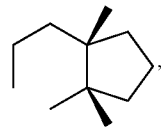
(XLI)

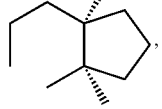
(XLII)

and $R_{35}$ stands for $C_1$-$C_4$-alkyl and most preferably methyl.

Suitable ditertiary diphosphines with heterocyclic skeletons are described in EP 0 770 085, by T. Benincori et al. in J. of Organomet. Chem. 529 (1997), pp. 445 to 453, and in J. Org. Chem., 61, p. 6244, (1996) by F. Bonifacio et al. in Chiratech 1997, 11th to 13 Nov. 1997, Philadelphia, Pa., USA, and by L. F. Tietze et al, Chem. Commun. pp. 1811-1812 (1999).

Some examples are

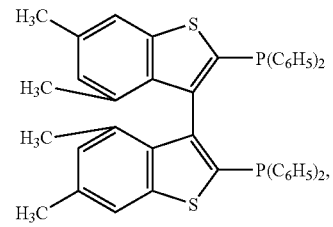

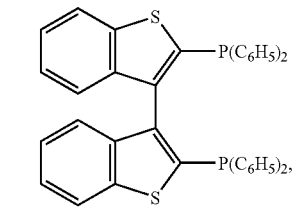

-continued

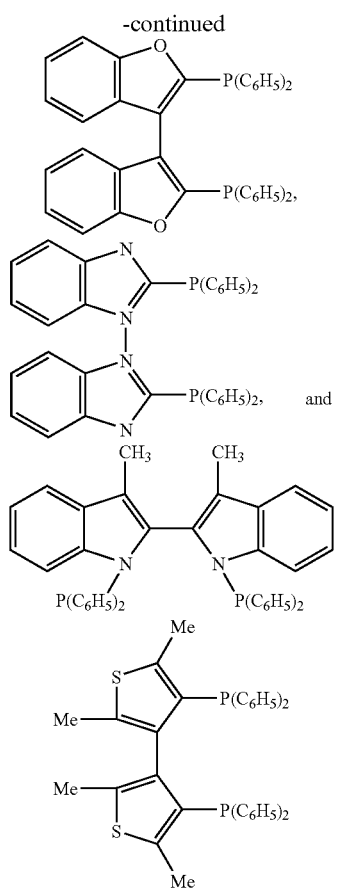

Achiral and chiral ditertiary diphosphines for water-soluble catalysts are likewise known and described in the literature. Such diphosphines contain one or more water-solubilising polar substituents which are attached to substituents of the phosphine group and/or to the skeleton diphosphine, either direct or via a bridging group. The diphosphines may be the same achiral and chiral ditertiary diphosphines as were defined earlier, including the preferences, which in addition contain water-solubilising polar substituents. Such ligandens are for example described by G. Papadogianakis et al. in James J. Spivey (Editor), Catalysis vol. 13, The Royal Society of Chemistry/Information Service (1997), pp. 115-193.

The polar substituents may be hydroxyl, and acid or ammonium groups. Examples of acid groups include carboxylic, sulphonic, sulphatic and phosphonic acid groups. Examples of ammonium include —$NH_3^+$ and secondary ammonium with 1 to 12, preferably 1 to 6 carbon atoms; tertiary ammonium with 2 to 24, preferably 2 to 12 carbon atoms; and quaternary ammonium with 3 to 36, preferably 3 to 18 carbon atoms; the ammonium groups contain an anion of an inorganic or organic acid.

One quite specifically preferred group of polar substituents is selected from the group comprising —OH, —$CO_2M_1$, —$SO_3M_1$, —O—$SO_3M_1$, —$PO(OM_1)_2$, and —$NR_{37}R_{38}R_{39}^+X_4^-$, where $M_1$ stands for H, an alkali metal cation or an ammonium cation, $R_{37}$, $R_{38}$ and $R_{39}$ independently of one another are H, $C_1$-$C_4$-alkyl, phenyl or benzyl, or $R_{37}$ and $R_{38}$ together are tetramethylene, pentamethylene or 3-oxapentylene, and $X_4$ is the anion of an inorganic or organic acid. Examples of acids from which the anion can be derived include HCl, HBr, HI, $H_2SO_4$, $C_1$-$C_8$-carboxylic acids, $C_1$-$C_8$-sulphonic acids, $C_1$-$C_8$-phosphonic acids, $HClO_4$, $HBF_4$, $HSbF_6$ and $HPF_6$. $M_1$ as an ammonium cation may satisfy the formula $^+NR_{37}R_{38}R_{39}R_{40}$, in which $R_{37}$, $R_{38}$, $R_{39}$ and $R_{40}$ independently of one another are H, $C_1$-$C_4$-alkyl, phenyl or benzyl, or $R_{37}$ and $R_{38}$ together are tetramethylene, pentamethylene or 3-oxapentylene. The phosphine groups may contain 1 to 4 polar substituents, with at least one radical of the phosphine group containing at least one polar substituent.

The invention also covers ditertiary diphosphines whose solubility in water is attained thanks to a covalent bond (direct or via a bridging group) from the diphosphine to the spine of a water-soluble polymer or oligomer, for example polyethylene glycol, polyvinyl alcohol and polyacrylic acid.

The bridging groups may be groups of the formula —$X_5$—$R_{41}$—, in which $X_5$ represents a direct bond, O, NH, Si CH N($C_1$-$C_4$-alkyl), NH—CO, N($C_1$-$C_4$-alkyl)CO, CO—NH, CON($C_1$-$C_4$-alkyl), NH—CO—O, N($C_1$-$C_4$-alkyl)CO—O, O—CO—NH, O—CON($C_1$-$C_4$-alkyl), NH—CO—NH, N($C_1$-$C_4$-alkyl)CO—NH or N($C_1$-$C_4$-alkyl)CO—N($C_1$-$C_4$-alkyl), and $R_{41}$ stands for a monovalent to tetravalent hydrocarbon radical with 1 to 40, preferably 1 to 30, and most preferably 1 to 20 carbon atoms, which may be interrupted one or more times with heteroatoms or heterogroups as stated earlier for $X_5$. Examples of hydrocarbon radicals include linear or branched $C_1$-$C_{18}$-alkylene, $C_5$- or $C_6$-cycloalkylene, $C_5$- or $C_6$-cycloalkylene-$C_1$-$C_6$-alkylene, $C_5$- or $C_1$-$C_6$-alkylene-$C_6$-cycloalkylene-$C_1$-$C_6$-alkylene, phenylene, phentriyl, $C_1$-$C_6$-alkylene-$C_6H_4$—, $C_1$-$C_6$-alkylene-$C_6H_4$—$C_1$-$C_6$-alkylene, and ($C_1$-$C_6$-alkylene)$_3$-$C_6H_3$—.

One preferred group of achiral and chiral diphosphines are those of formulas V to XXIII and most preferably diphosphines of formulas XXIV to XL, in which $R_{10}$ to $R_{36}$ have the meanings stated earlier, $R_4$, $R_5$, $R_7$ and $R_8$ are identical and like the two Rs stand for a radical of the formula

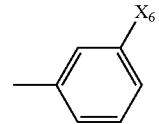

in which $X_6$ represents —$SO_3M_1$, —$CO_2M_1$, —$C_1$-$C_4$-alkylene-$SO_3M_1$, —$C_1$-$C_4$-alkylene-$CO_2M_1$, —N($C_1$-$C_4$-alkyl)$_2$ or $^+N(C_1$-$C_4$-alkyl)$_2X_4^-$, $M_1$ denotes H, Na or K, and $X_4$ stands for Cl, Br or I.

Some examples of polymeric water-soluble diphosphines are described in EP-0 329 043 and WO 98/01457, and by W. D. Muller et al. in Chem. Commun., (1996), pp. 1135-1136.

A further preferred group of water-soluble diphosphines are those of formula XLIII, $(M_1O_2O—CH_2CH_2—O—CH_2)_3—NR_{42}—R_{41}$ (XLIII)

in which $M_1$ stands for H, an alkali metal cation or an ammonium cation, $R_{42}$ denotes $C_1$-$C_4$ alkyl and preferably H, and $R_{41}$ is the monovalent radical of a chiral ditertiary diphosphine, the CO group being directly attached to a carbon or nitrogen atom of the diphosphine skeleton, or to an oxygen or nitrogen atom or to a carbon atom of a bridging group of the diphosphine skeleton. Examples of suitable bridging groups include —O—, —NH—, $C_1$-$C_6$-alkylene-, —N($C_1$-$C_4$-alkyl)-, —O—$C_1$-$C_6$-alkylene-, —NH—$C_1$-$C_6$-alkylene- and —N($C_1$-$C_4$-alkyl)-$C_1$-$C_6$-alkylene-. For $M_1$ the embodiments and preferences stated earlier apply.

One preferred sub-group of the diphosphines of formula XLIII are those of formula XLIIIa

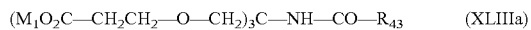
(XLIIIa)

in which $M_1$ has the meanings stated earlier, and $R_{43}$ denotes a radical of the formulas

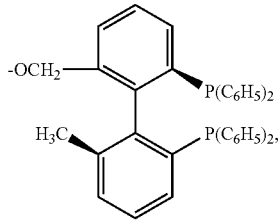

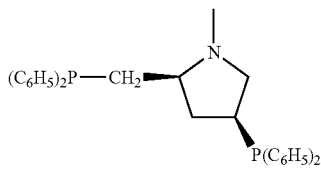

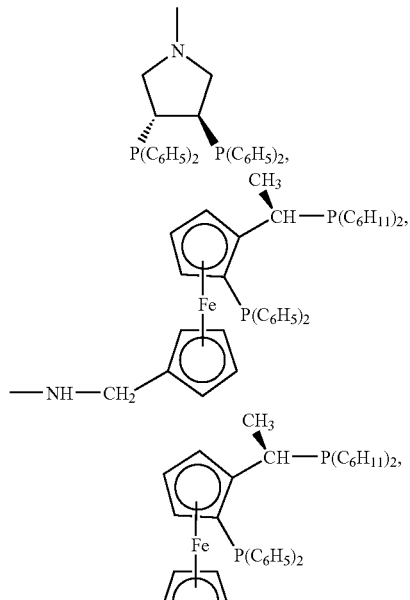

A further example of water-soluble ferrocenyl diphosphines is the compound of the formula

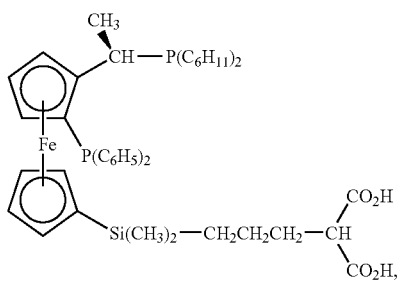

which is described in WO 98/01457.

Also included are compounds of the following form

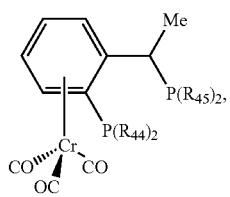

where $R_{44}$ and $R_{45}$ are the same or different and stand for phenyl, o-tolyl, p-tolyl, m-tolyl, butyl, propyl, xylyl, cyclohexyl, or

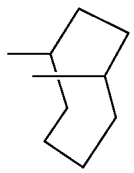

phoban

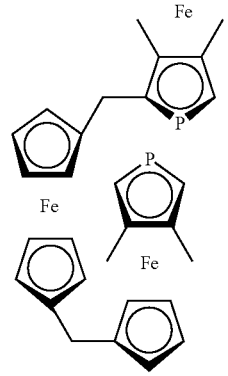

or compounds of the form

The diphosphines of formulas XLIII and XLIIIa are novel and can be obtained in the following manner. The known amine (HO₂C—CH₂CH₂—O—CH₂)₃C—NH₂, or rather its alkyl ester, can be reacted with carboxyl groups of a corresponding ditertiary diphosphine to give the amide. The amine can be derivatised to give the isocyanate or a capped isocyanate (for example with carbonyl diimidazol), which can be reacted with OH or NH groups of a corresponding ditertiary diphosphine, forming urethane or urea bridges.

The catalysts or catalyst precursors used in accordance with the invention may be metal complexes of the formulas XLIV, XLIVa and XLIVb,

[X₇Me₂YZ]  (XLIV),

[X₇Me₂Y]⁺A₂⁻  (XLIVa),

[X₇Ru(II)X₈X₉]  (XLIVb), in which

Y stands for two monoolefin ligands or a diene ligand;

X₇ represents an achiral or chiral ditertiary diphosphine that forms a 5 to 7 membered ring with the metal atom Me₂ or Ru;

Me₂ denotes Ir(I) or Rh(I);

Z represents —Cl, —Br or —I; and

A₂ is the anion of an oxy-acid or complex acid,

X₈ and X₉ are the same or different and have the meaning of Z and A₂, or X₈ and

X₉ stand for allyl or 2-methylallyl, or X₈ has the meaning of Z or A and X₉ stands for hydride.

Preferred are metal complexes in which Y stands for 1,5-hexadiene, 1,5-cyclooctadiene or norbornadiene. In the metal complexes according to the invention Z preferably stands for —Cl, —Br or —I. In preferred metal complexes A₂ stands for ClO₄—, CF₃SO₃⁻, CH₃SO₃⁻, HSO₄⁻, BF₄⁻, B(phenyl)₄⁻, PF₆⁻, SbCl₆⁻, AsF₆⁻ or SbF₆⁻.

Further suitable ruthenium complexes are known in the literature and are for example described in U.S. Pat. No. 4,691,037, U.S. Pat. No. 4,739,085, U.S. Pat. No. 4,739,084, EP 0 269 395, EP 0 271 310, EP 0 271 311, EP 0 307 168, EP 0 366 390, EP 0 470 756, JP 08 081 484, JP 08 081 485, JP 09 294 932, EP 0 831 099, EP 0 826 694, EP 0 841 343, J. P. Genêt, Arcos Organics Acta, 1 (1995) 4, N. C. Zanetti et al., and Organometallics 15 (1996) 860.

The metal complexes of formulas XLIV, XLIVa or XLIVb are prepared using methods known in the literature. Their preparation is for example described in EP-0 564 406. The catalysts, or catalyst precursors, may be added as isolated compounds to the reaction mixture. It has proved advantageous to prepare the catalysts, or catalyst precursors, with or without solvents in situ before the conversion and then combine them with the reaction mixture for the conversion.

In detail the process can be carried out by first preparing the catalyst and then adding the catalyst to a solution or suspension of the pterins that are to be hydrogenated, for example folic acid or carboxylic acid salts thereof, folic acid esters or folic acid ester salts, or vice versa. Hydrogen is pressed on in an autoclave and in this manner a protecting gas which has usefully been employed is removed. The reaction mixture is heated if necessary and then hydrogenated. Once the reaction has finished the mixture is cooled down if necessary and the autoclave is relaxed. The reaction mixture may be forced out of the reactor using, for example, nitrogen and the hydrogenated reaction product isolated in a per se known manner, for example by means of extraction, precipitation and crystallisation, or it may be reacted further in situ. It was observed that (6S,αS) and (6S,αR) tetrahydrofolic acid esters and (6S,αR) tetrahydrofolic acid ester salts are already able to precipitate during the hydrogenation process, which can considerably facilitate their isolation from the reaction mixture.

It is particularly advantageous if folic acid is employed, and an esterification and hydrogenation are carried out consecutively in a reaction vessel. It is helpful to use the same solvent for the esterification in the presence of an acid HA as was used for the hydrogenation, notably the alcohol, for example methanol or ethanol, with which the folic acid is also esterified.

In another advantageous process variant the esterification of the folic acid and the hydrogenation take place simultaneously, the tetrahydrofolic acid ester and salts thereof being formed in situ and simultaneously hydrogenated. To this end all the components (folic acid, alcohol, solvent, acid HA and the catalyst) are put into a reaction vessel, hydrogen is pressed on and the hydrogenation is carried out. It is helpful if the solvent is the same as the alcohol, for example methanol or ethanol, that is used for esterification.

The hydrogenation may be carried out continuously or batchwise in various types of reactors. Reactors that permit comparatively thorough blending and good heat dissipation, such as for example circulating reactors, are preferred. This type of reactor has proved to be particularly effective when using small quantities of catalyst.

Conventional methods may be employed to isolate desired diastereomers of tetrahydropterin derivatives, for example (6S,αS) tetrahydrofolic acid or tetrahydrofolic acid salts, (6S,αS) tetrahydrofolic acid esters and (6S,αR) tetrahydrofolic acid ester salts, for example chromatographic methods or fractionated crystallisation, it being possible to carry out a derivitisation beforehand in a per se known manner. Tetrahydrofolic acid esters and tetrahydrofolic acid ester salts offer the advantage that the separation of the diastereomers may also be carried out with organic solvents the first time and surprisingly a high concentration of the (6S,αS) and (6S,αR) diastereomers, respectively, is observed in the crystallisate and of the (6R,αS) and (6R,αR) diastereomers, respectively, in the mother liquor. The tetrahydrofolic acid can be obtained in conventional manner from tetrahydrofolic acid esters and tetrahydrofolic acid ester salts by hydrolysis.

It is helpful if the isolation of tetrahydrofolic acid esters and tetrahydrofolic acid ester salts from alcoholic reaction media is done by crystallisation. Surprisingly it has been found that (6S,αS) and (6S,αR) diastereomers crystallise superbly and the crystallisate has very high concentrations of these diastereomers. Thus, for instance, in the case of the tetrahydrofolic acid dimethylester sulphonic acid addition salts a (6S,αS) to (6R,αS) diastereomer ratio of 99:1 was found in the first crystallisate. Conversely, the (6R,αS) and (6R,αR) diastereomers are then concentrated in the mother liquor. It is also surprising that the crystallisate contains virtually no catalyst, with the result that the (6S,αS) and (6S,αR) diastereomers are obtained in a very high degree of purity.

The formula III compounds with organic acids HA in the form of their pure (αS) and (αR) enantiomers or mixtures in any desired mixing ratios are novel and constitute a further subject-matter of the invention. For R₁, R₂, HA and x the embodiments and preferences stated earlier in respect of formula III compounds apply. It is preferred if in formula III R₁ and R₂ are each methyl or ethyl.I, HA preferably stands for benzene sulphonic acid or toluene sulphonic acid, and x is preferably the number 1, or a fractionated number between 0.5 and 1.5.

A further subject-matter of the invention is tetrahydrofolic acid ester salts in the form of their pure diastereomers and mixtures thereof in any desired mixing ratios, which satisfy formula IIIa,

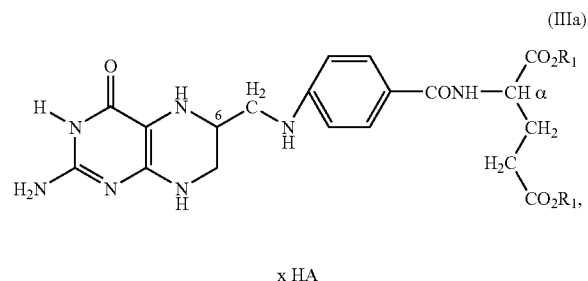

(IIIa)

x HA in which $R_1$ or $R_2$ are H, and one of $R_1$ or $R_2$, or both $R_1$ and $R_2$ independently of one another represent a monovalent hydrocarbon radical or a heterohydrocarbon radical attached via a carbon atom with heteroatoms selected from the group comprising —O—, —S— and —N—, HA stands for a monobasic to tribasic inorganic or organic acid, and x denotes an integer from 1 to 6 or a fractional number between 0 and 6. For $R_1$, $R_2$, HA and x the embodiments and preferences stated earlier in respect of formula III compounds apply. It is especially preferred if $R_1$ and $R_2$ in formula III are each methyl or ethyl, HA preferably stands for benzene sulphonic acid or toluene sulphonic acid, and x is preferably the numbers 1 or 2, or a fractional number between 0.5 and 2.

A further subject-matter of the invention is

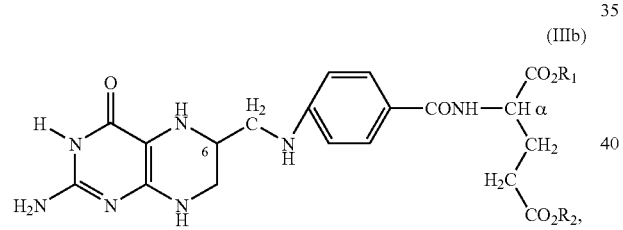

(IIIb)

in which $R_1$ or $R_2$ are H, and one of $R_1$ or $R_2$, or both $R_1$ and $R_2$ independently of one another represent a monovalent hydrocarbon radical or heterohydrocarbon radical attached via a carbon atom with heteroatoms selected from the group comprising —O—, —S— and —N—. For $R_1$ and $R_2$ the embodiments and preferences stated earlier in respect of formula III compounds apply. It is preferred if $R_1$ and $R_2$ each represent $C_1$-$C_{12}$ alkyl and particularly $C_1$-$C_4$ alkyl, for example methyl or ethyl. The compounds of formula IIIb can be obtained by treating formula IIIa compounds with bases.

In the case of the processes being described, the degree of optical concentration may be dependent on the additives that are present, the solvent used, the temperature and the concentration. The optimal process conditions adapted to the particular objective can be determined by simple experimentation.

The examples which follow can be carried out with similar success by replacing the generically or specifically outlined reactants and/or process conditions of this invention with ones set out in the following examples. Similarly, the following specific embodiments are to be viewed as purely exemplary and in no way limiting the remainder of the disclosure.

The overall disclosure includes all applications, patents and publications cited in this text by virtue of making reference thereto.

On the basis of the foregoing description it will be possible for anyone skilled in the art to readily deduce the decisive elements of the invention and, without deviating from the underlying concept and the scope of the invention, to make alterations and supplements to it and thereby adapt the invention to different needs and conditions.

The optical yield, or the ratio of the (6S,αS) diastereomer to the (6R,αS) diastereomer or of the (6S,αR) diastereomer to the (6R,αR) diastereomer of the tetrahydrofolic acid esters and tetrahydrofolic acid ester salts, is determined in the following manner using high-pressure liquid chromatography (HPLC) directly in the reaction mixture:

15 mg of the reaction solution are dissolved in 1 ml of solvent which is prepared from 6.8 g of β-cyclodextrin and 270 ml of 37% formaldehyde in 1000 ml of water. The separation is done by means of a 5 mm, 240×4 mm Nucleosil C-8 column manufactured by the firm Macherey-Nagel and a mobile solvent prepared in the following manner: 6.8 g of β-cyclodextrin are dissolved in a mixture of 8.5 ml of triethylamine, 850 ml of water and 150 ml of acetonitrile. The pH of the solution is adjusted by addition of acetic acid to a pH of 7.5, and a further 270 ml of 37% formaldehyde are added. The detection of the two diastereomers takes place at a wavelength of 300 nm.

The following abbreviations are used for the ditertiary diphosphines employed:

a hydrogenations in alcoholic reaction medium

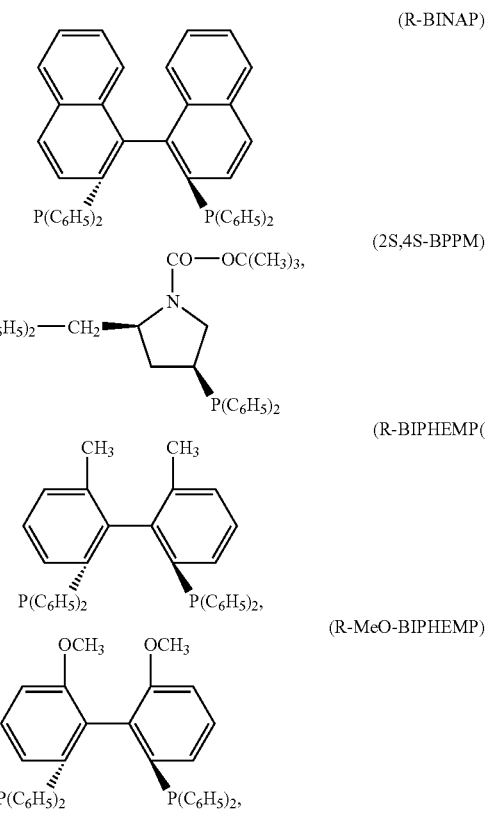

-continued
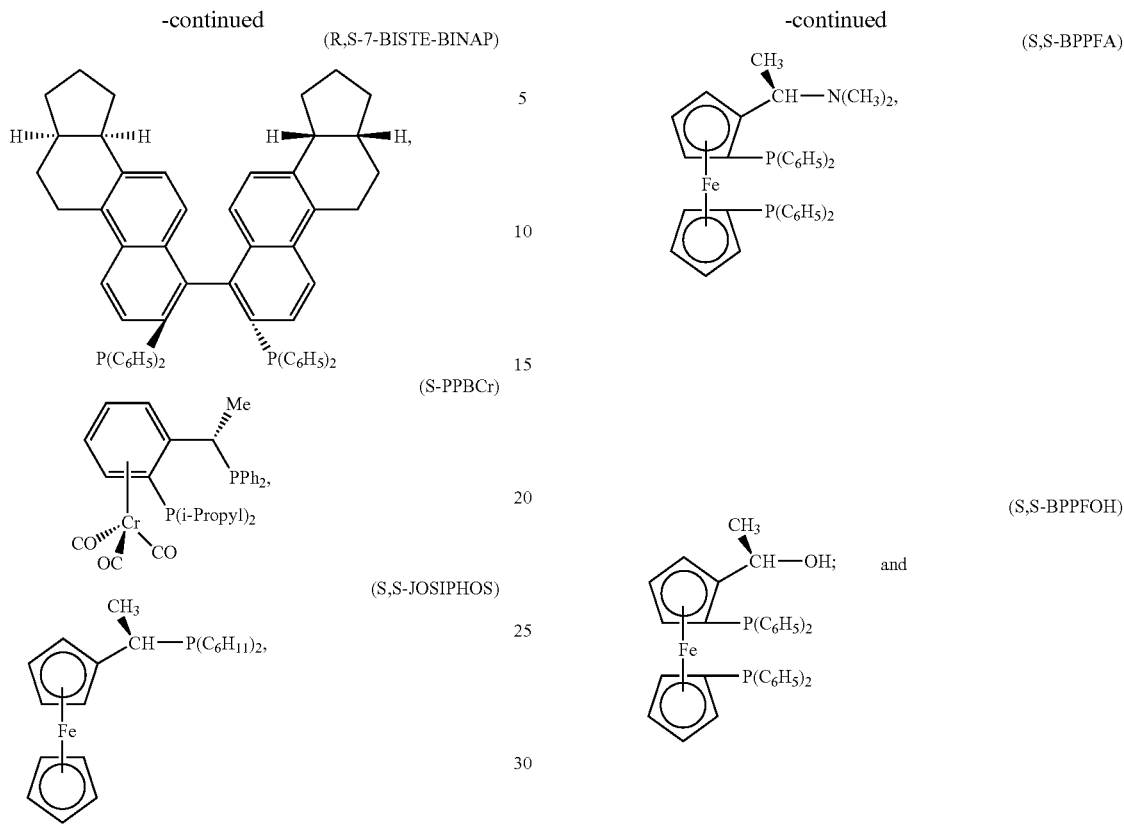
b hydrogenations in aqueous reaction medium
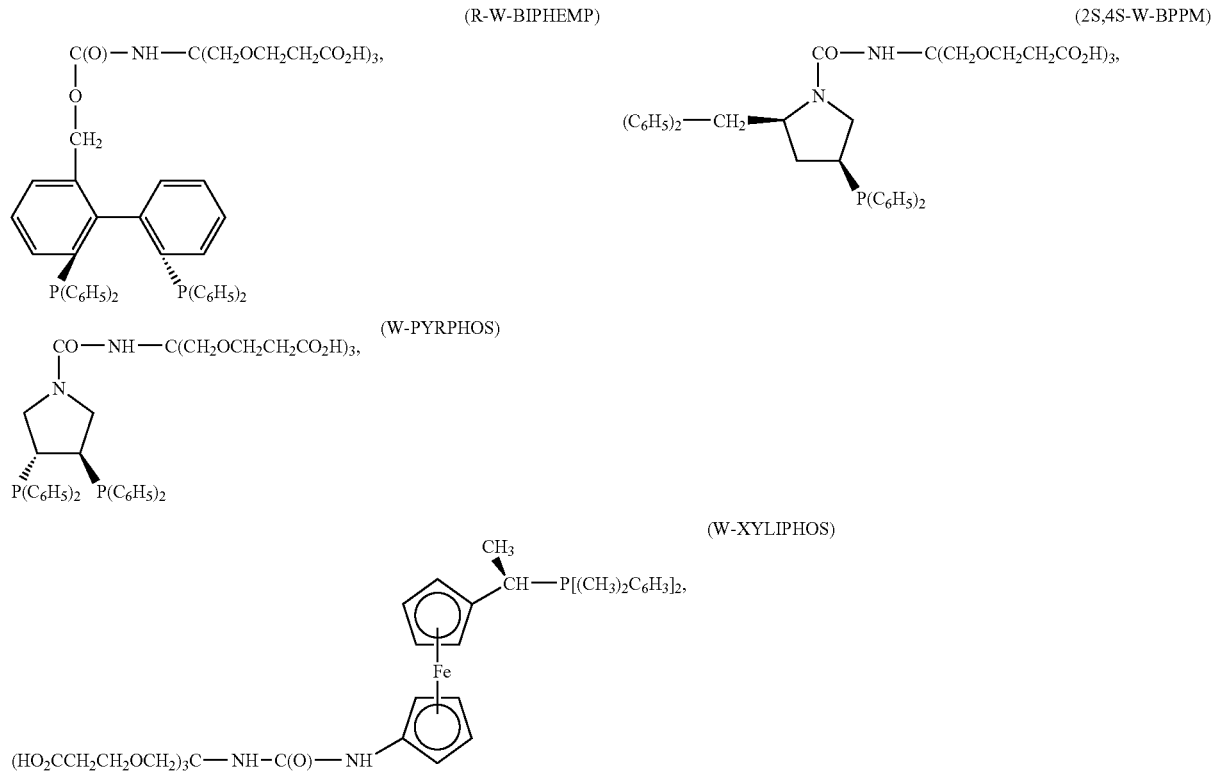

-continued
(PA-JOSIPHOS)

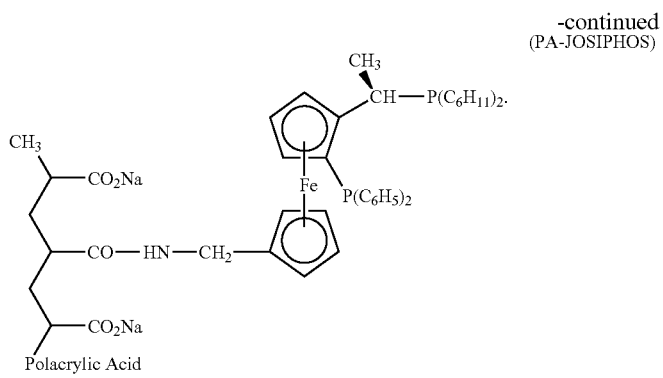

Polacrylic Acid

The preparation of the catalysts and of the hydrogenating solutions, the transfer of the solutions and suspensions, as well as the hydrogenation operations, take place under exclusion of oxygen. The Schlenk technique can be employed, with which anyone skilled in the art will be familiar. Solvents and autoclaves that have been degassed and gassed with a protecting gas, such as for example nitrogen or inert gases (helium, neon, argon or krypton) are used. The hydrogenation reactions are carried out in steel autoclaves with a magnetic stirrer or gassing agitator.

EXAMPLES

A Preparation of Folic Acid Ester Salts

Example A1

(αS) Folic Acid Dimethylester Benzene Sulphonate 800 g (αS) of folic acid dihydrate (1.68 mole) are charged at 40° C. into a solution of 530 g of benzene sulphonic acid (3.35 mmoles) and 20 liters of anhydrous methanol in a nitrogen atmosphere. The mixture is heated for half an hour with refluxing, cooled down and concentrated by evaporation to a volume of 5 liters. The separated product is filtered off by suction, washed with 1 liter of methanol and dried in a drying chamber at 40° C. and 20 mbars. 966 g of (αS) folic acid dimethylester benzene sulphonate are obtained (1.45 mole, 86% of theoretical yield) The product contains 26.2% benzene sulphonic acid, 1.67% water and 2.26% methanol.

The substance breaks down above 150° C.

$^1$H-NMR in DMSO-$d_6$: 8.78 (1H, s), 8.46 (2H, bs), 8.32 (1H, d), 7.64-7.68 (m), 7.35-7.40 (m), 6.66 (2H, d), 0.8 (2H, s), 4.39 (1H, m), 3.62 (3H, s), 3.57 (3H, s), 2.42 (2H, m), 1.98-2.11 (2H, m).

Example A2

(αS) Folic Acid Diethylester Benzene Sulphonate 8 g of (αS) folic acid dihydrate (16.76 mmoles) are charged into a solution of 3.18 g of benzene sulphonic acid (20.11 mmoles) and 1.5 liters of anhydrous ethanol. The solution is heated for 5 hours with refluxing, cooled down to room temperature and after 12 hours the separated product is filtered off by suction. After drying at 40° C. and 20 mbars, 10.09 g of (αS) folic acid dimethylester benzene sulphonate are obtained (15.29 mmoles, 92% of theoretical yield). The product contains 21.8% benzene sulphonic acid).

The substance breaks down above 150° C.

$^1$H-NMR in DMSO-d6: 8.77 (1H, s), 8.27 (3H, d, bs), 7.66 (m), 7.35 (m), 6.66 (2H, d), 4.59 (2H, s), 4.37 (1H, m), 3.98-4.13 (4H, m), 2.40 (2H, m) 1.97-2.06 (2H, m) 1.06-1.21 (6H, m).

B Preparation of Water-Soluble Ditertiary Diphosphines

Example B1

Preparation of 2S,4S—W-BPPM a Preparation of The Triester

A solution of 377 mg (0.83 mmole) of 2-diphenylphosphinomethyl-4-β-phenylphosphino pyrrolidine (PPM) in 2.5 ml of toluene is added to a solution in accordance with Example A1 (1.1 mmole of isocyanate triester) and the mixture is stirred overnight. After concentrating by evaporation on a rotary evaporator and partially removing the toluene at reduced pressure, the raw product is purified chromatographically (silica gel: Merck 60; mobile solvent: ethyl acetate). 605 mg of product are obtained (yield: 81%).

b Preparation of the Triacid 1 ml of water and 0.6 g of KOH are added to a solution of 590 mg of the triester in accordance with Example B1a in 5 ml ethanol, and the mixture is stirred for 3 hours. The ethanol is then evaporated off at reduced pressure and the mixture dissolved in 25 ml of water. Next the solution is acidified with 2 n of HCl and extracted several times with ethyl acetate. The organic phases are collected, washed with water, dried over sodium sulphate and finally evaporated to dryness at reduced pressure. The product is obtained as a white solid in an 88% yield.

Example B2

Preparation of W-PYRPHOS a Preparation of the Triester

The same procedure as in Example B1a is followed, but using 3,4-diphenylphosphino pyrrolidine (Pyrphos) as the starting compound. The reaction product is obtained in a 63% yield.

b Preparation of the Triacid

The same procedure as in Example B1b is followed. The product is obtained as a white solid in a 95% yield.

Example B3

Preparation of R—W-BIPHEMP a Preparation of the Triester

The same procedure as in Example B1a is followed, but using 2,2'-diphenylphosphino-5-methyl-5'-hydroxymethyl (HO-Biphemp) as the starting compound. The reaction product is obtained in an 82% yield.

b Preparation of the Triacid

The same procedure as in Example B1b is followed. The product is obtained as a white solid in a 92% yield.

Example B4

Preparation of W-XYLIPHOS a Preparation of the Triester

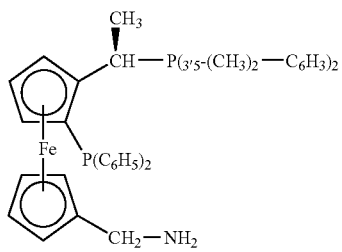

(amine ligand A, see WO 98/01457),

A solution of 1 g (1.5 mmole) of amine ligand A in 8 ml of methylene chloride is added at 0° C. to an equimolar amount of carbonyl diimidazole in 6 ml of methylene chloride and the reaction mixture is then stirred for 2 hours at room temperature. 1.6 equivalents of $H_2N-C(CH_2-O-CH_2CH_2C(O)-OCH_2CH_3$ and 5 mg of dibutyltin dilaurate are next added and the mixture is stirred for 48 hours at 50° C. After chromatographic purification (silica gel: Merck 60; mobile solvent: hexane/ethyl acetate, 1:1) the product is obtained as a nearly solid, orange oil in a 65% yield.

b Preparation of the Triacid:

1 g of diphosphine triester is dissolved in 10 ml of ethanol and 1 ml of 20% aqueous KOH solution is added. After stirring for 2 hours the ethanol is evaporated off at reduced pressure and the product is dissolved in 20 ml of water. By addition of 2 n of HCl the product is precipitated, filtered off, washed several times with water and finally dried at 50° C. under a high vacuum. The product is obtained as an orange-yellow solid in a 92% yield.

Example B5

Preparation of PA-JOSIPHOS

The ligand is prepared as in Example B25 of WO 98/01457. MW: 1480.

C Hydrogenations in Alcoholic Reaction Medium

Examples C1-C29

Method A 6.72 mg of $[Ir(COD)Cl]_2$ (10 μmoles) and diphosphine ligand (25 μmoles) are weighed, degassed and dissolved in dichloromethane. Dichloromethane is condensed off under a high vacuum and the residue is taken up in 5 ml of methanol. 1.25 g of (αS) folic dimethylester benzene sulphonate as in Example A1 (2 mmoles) are suspended in 25 ml of methanol and added to the catalyst. The suspension is added in a nitrogen countercurrent to a 100 ml autoclave and hydrogenated until there is no longer any hydrogen uptake. COD stands for cyclooctadiene.

Method B 8.12 mg of $[Rh(COD)_2]BF_4$ (20 μmoles) and diphosphine ligand (25 μmoles) are weighed, degassed and dissolved in a mixture of tetrahydrofuran and methanol. The solvents are condensed off under a high vacuum and the residue is taken up in 5 ml of methanol. 1.25 g of (αS) folic acid dimethylester benzene sulphonate as in Example A1 (2 mmoles) are suspended in 25 ml of methanol and added to the catalyst. The suspension is added in a nitrogen countercurrent to a 100 ml autoclave and hydrogenated until there is no longer any hydrogen uptake.

The hydrogenations are carried out at a temperature of 70° C. (25° C. in Example C9) and a pressure of 80 bars (20 bars in Examples C9 and 010). The results are given in Table 1.

Example C25

28.79 g of (αS)folic acid dihydrate (60 mmoles) are weighed into a 1 l autoclave and degassed. 121.82 mg of $[Rh(COD)_2]BF_4$ (300 μmoles) and 233.51 mg of R-BINAP (375 μmoles) are weighed, degassed and dissolved in a mixture of tetrahydrofuran and methanol. The solvents are condensed under a high vacuum and the residue is taken up in 50 ml of methanol. 9.49 g of anhydrous benzene sulphonic acid (60 mmoles) are dissolved in 200 ml of methanol and added to the autoclave in a nitrogen countercurrent. A further 550 ml of methanol are added, and also the catalyst solution. Hydrogenation is carrried out at 70° C. and 20 bars hydrogen pressure for 15 hours. The conversion rate into tetrahydrofolic dimethylester benzene sulphonate is 80%. The ratio of the diastereomers (6S,αS):(6R,αS) is 71:28.

Example C26

16.68 mg of $Ru(BINAP)(2\text{-methylallyl})_2$ (20 μmoles) (prepared as per J. P. Genet et al, Tetrahedron Asymmetry, vol. 5, No. 4, pp. 665-674, 1994) are suspended in 5 ml of degassed methanol and a suspension of 1.25 g of (αS) folic acid dimethylester benzene sulphonate as per Example A1 (2 mmoles) in 25 ml of methanol is added. The suspension is transferred in a nitrogen countercurrent to a 100 ml autoclave and hydrogenated for 17 hours at 70° C. and 80 bars hydrogen pressure. The conversion rate into tetrahydrofolic acid dimethylester benzene sulphonate is 30%. The ratio of the diastereomers (6S,αS):(6R,αS) is 62:37.

Example C27

8.12 mg of $[Rh(COD)_2]BF_4$ (20 μmoles) and 15.57 mg of BINAP (25 μmoles) are weighed, degassed and dissolved in a mixture of tetrahydrofuran and methanol. The solvents are condensed off under a high vacuum and the residue is taken up in 5 ml of methanol. A suspension of 0.39 g of 6-hydroxymethyl pterin (2 mmoles) (prepared as per P. H. Boyle et al., Chem. Ber.; vol. 113, page 1514, 1980) and 0.32 g of benzene sulphonic acid (2 mmoles) in 25 ml of methanol is added to the catalyst. The mixture is added in a nitrogen countercurrent to a 100 ml autoclave and hydrogenated at 70° C. and 80 bars hydrogen pressure for 15 hours. The conversion rate to 6-hydroxymethyl-5,6,7,8-tetrahydropterin is 85% and is determined by HPLC direct from the reaction solution. The HPLC method employed is the same one as is used for the quantitative determination of the tetrahydrofolic acid.

Example C28

8.12 mg of [Rh(COD)$_2$]BF$_4$ (20 µmoles) and 15.57 mg of BINAP (25 mmoles) are weighed, degassed and dissolved in a mixture of tetrahydrofuran and methanol. The solvents are condensed off under a high vacuum and the residue is taken up in 5 ml of methanol. A suspension of 0.48 g of 6-phenylpterin (2 mmoles) (prepared as per H. Yamamoto et al., Chem. Ber.; vol. 106, page 3175, 1973) and 0.32 g of benzene sulphonic acid (2 mmoles) in 25 ml of methanol is added to the catalyst. The mixture is added in a nitrogen countercurrent to a 100 ml autoclave and hydrogenated at 70° C. and 80 bars hydrogen pressure for 15 hours. The conversion rate to 6-phenyl-5,6,7,8-tetrahydropterin is 64% and is determined by HPLC direct from the reaction solution. The HPLC method employed is the same one as is used for the quantitative determination of the tetrahydrofolic acid.

Example C29

8.12 mg of [Rh(COD)$_2$]BF$_4$ (20 mmoles) and 15.57 mg of BINAP (25 mmoles) are weighed, degassed and dissolved in a mixture of tetrahydrofuran and methanol. The solvents are condensed off under a high vacuum and the residue is taken up in 5 ml of methanol. A suspension of 0.35 g of 6-methylpterin (2 mmoles) (prepared as per P. Waring et al., Aust. J. Chem. vol. 38, page 629, 1985) and 0.32 g of benzene sulphonic acid (2 mmoles) in 25 ml of methanol is added to the catalyst. The mixture is added in a nitrogen countercurrent to a 100 ml autoclave and hydrogenated at 70° C. and 80 bars hydrogen pressure for 15 hours. The conversion rate to 6-methyl-5,6,7,8-tetrahydropterin is 63% and is determined by HPLC direct from the reaction solution. The HPLC method employed is the same one as is used for the quantitative determination of the tetrahydrofolic acid.

TABLE 1

| Example | Metal | Additive | Ligand | S/C | Solvent | Convrsn rate | Ratio (6S,αS):(6R,αS) | Method |
|---|---|---|---|---|---|---|---|---|
| C1 | Ir | — | R-BINAP | 100 | MeOH | 80% | 65:35 | A |
| C2 | Ir | Bu$_4$NI | (2S,4S)-BPPM | 100 | MeOH | 80% | 62:38 | A[1] |
| C3 | Ir | LiCl | (2S,4S)-BPPM | 100 | MeOH | 90% | 30:70 | A[2] |
| C4 | Ir | — | S,S-BPPFA | 100 | MeOH | 60% | 67:33 | A |
| C5 | Rh | — | R-BINAP | 100 | MeOH | 72% | 74:26 | B |
| C6 | Rh | NaI | R-BINAP | 100 | MeOH | 85% | 67:33 | B[3] |
| C7 | Rh | — | R-BINAP | 100 | MeOH | 70% | 71:29 | B[4] |
| C8 | Rh | — | R-BINAP | 100 | EtOH | 80% | 76:24 | B[5] |
| C9 | Rh | — | R-BINAP | 100 | i-PrOH | 20% | 80:20 | B[6] |
| C10 | Rh | — | R-BINAP | 100 | 1,2-propane diol | 62% | 75:25 | B[7] |
| C11 | Rh | | R-BINAP | 100 | Ethylene glycol | 56% | 78:22 | B[8] |
| C12 | Rh | — | R-BINAP | 100 | MeOH | 90% | 73:27 | B |
| C13 | Rh | — | R-BINAP | 200 | MeOH | 90% | 72:28 | B[9] |
| C14 | Rh | — | R-BINAP | 100 | MeOH/THF/1:1 | 90% | 72:28 | B[10] |
| C15 | Rh | — | R-BINAP | 700 | MeOH | 60% | 69:31 | B[11] |
| C16 | Rh | — | S-PPBCr | 100 | MeOH | 70% | 71:29 | B |
| C17 | Rh | — | S,S-BPPFOH | 100 | MeOH | 90% | 58:42 | B |
| C18 | Rh | — | (2S,4S)-BPPM | 100 | MeOH | 90% | 68:32 | B |
| C19 | Rh | — | S,S-JOSIPHOS | 100 | MeOH | 60% | 61:39 | B |
| C20 | Rh | — | R-BIPHEMP | 100 | MeOH | 80% | 71:29 | B |
| C21 | Rh | — | R-MeO-BIPHEP | 100 | MeOH | 80% | 69:31 | B |
| C22 | Rh | — | R,S-7-BISTE-BINAP | 100 | MeOH | 90% | 71:29 | B |
| C23 | Ir | Pa | R-BINAP | 100 | MeOH/THF, 1:1 | 90% | 72:28 | A[12] |
| C24 | Rh | — | 1,2-bis(diphenyl-phosphino)ethane | 100 | MeOH | 90% | 51:49 | B |

Legend:
Bu stands for butyl, MeOH for methanol, EtOH for ethanol, i-PrOH for isopropanol and THF for tetrahydrofuran, Pa for parabanic acid.
[1] In this experiment 73.9 mg of tetrabutylammonium iodide (0.2 mmole) are added to the catalyst.
[2] In this experiment 8.48 mg of lithium chloride (0.2 mmole) are added to the catalyst.
[3] In this experiment 29.98 mg of sodium iodide (0.2 mmole) are added to the catalyst.
[4] In this experiment 3.55 g of (αS) folic acid diemethylester benzene sulphonate (566 mmoles) are reacted as per Method B in the stated solvent volumes, resulting in a 15% substrate concentration.
[5] In this experiment 1.31 g of (αS) folic acid diethylester benzene sulphonate (2 mmoles) were reacted as per Method B in ethanol to give tetrahydrofolic acid diethylester benzene sulphonate.
[6] In this experiment the hydrogenation of the folic acid dimethylester benzene sulphonate is carried out in 30 ml of i-propanol
[7] In this experiment the hydrogenation of the folic acid dimethylester benzene sulphonate is carried out in 30 ml of 1,2-propane diol.
[8] In this experiment the hydrogenation of the folic acid dimethylester benzene sulphonate is carried out in 30 ml of ethylene glycol.
[9] In this experiment the catalyst is prepared from 4.06 mg of [Rh(COD)$_2$]BF$_4$ (10 µmoles) and 7.78 mg of R-BINAP (12.5 µmoles).
[10] In this experiment the hydrogenation is carried out in a mixture of 15 ml of THF and 15 ml of MeOH.
[11] In this experiment the catalyst is prepared from 1.16 mg of [Rh(COD)$_2$]BF$_4$ (2.86 µmoles) and 2.22 mg of R-BINAP (3.57 µmoles).
[12] In this experiment 4.56 mg of parabanic acid (40 mmoles) are added to the catalyst. The hydrogenation is carried out in MeOH/THF (1:1).

D Hydrogenations in Aqueous Reaction Medium

Examples D1-D8

0.0025 mmole of ligand is dissolved in 5 ml of water and 0.5 ml of pH 7 buffer (0.041 mole of $Na_2HPO_4$ and 0.028 mmole of $KH_2PO_4$ in 1 l of water). The carboxylic acid groups of the ligands are then reacted with 0.1N of NaOH until a clear solution is produced. The resulting solution is added to 7.4 mg (0.02 mmole) of $[Rh(NBD)_2]BF_4$ and stirred until a solution has formed (NBD is norbornadiene). This solution is added to a solution of 2 mmoles of (αS) folic acid disodium salt in 11 ml of water and 1.5 ml of pH 7 buffer and the mixture transferred in an argon countercurrent with the aid of a cannula to a hydrogenating autoclave with gassing stirrer. The autoclave is sealed, the argon exchanged for hydrogen, and lastly hydrogen is pressed on until the desired pressure is reached. The hydrogen pressure is maintained from the reserve vessel via a reducing valve. The hydrogenation process is started up by switching on the stirrer. In the following Table 2 the stated hydrogenation time is the time it takes for the reaction to come to a standstill (no more hydrogen uptake). Unless indicated otherwise, this corresponds to complete conversion of the (αS) folic acid. The pressure is 80 bars and the reaction temperature 70° C. (30° C. in Example D6). The molar ratio of substrate to catalyst (S/C) is 100 in Examples D1-D7 and 1000 in Example D8. The results are summarised in Table 2.

TABLE 2

| Example No. | Ligand | Time (hours) | Ratio (6S,αS):(αR,αS) | Observations |
|---|---|---|---|---|
| D1 | (S,R)-PA-JOSIPHOS | 17.5 | 68:32 | 25% (αS) folic acid |
| D2 | (2S,4S)-W-BPPM | 4 | 73.4:27.6 | |
| D3 | (3R,4R)-PYRPHOS | 2 | 59:41 | |
| D4 | (R)-W-BIPHEMP | 3.2 | 73:27 | |
| D5 | (S,R)-W-XYLIPHOS | 0.5 | 66:34 | |
| D6 | (S,R)-W-XYLIPHOS | 12 | 74.4:25.6 | |
| D7 | (S,R)-W-XYLIPHOS | 0.6 | 68:32 | Hydrogenation of (αS) folic acid suspension at pH 6.3[1)] |
| D8 | (S,R)-W-XYLIPHOS | 4 | 65:35 | S/C 1000[2)] |

Legend:
[1)] pH 6 buffer: 0.01 mole of $Na_2HPO_4$ and 0.071 mole of $KH_2PO_4$ in 1 l of water; when the reaction ends a further 4 ml of 1 N $KH_2PO_4$ is added.
[2)] 5 mmoles of (αS) folic acid disodium salt, 0.005 mmole of $[Rh(NBD)_2]BF_4$ and 0.00675 mmole of ligand are employed in a total of 16 ml of water and 2 ml of pH 7 buffer.

E Isolation of Tetrahydrofolic Acid Dimethylester Benzene Sulphonate and Tetrahydrofolic Acid Benzene Sulphonate Example E1: from Reaction C1 a Isolation Of Tetrahydrofolic Acid Dimethylester Benzene Sulphonate

The reaction solution from reaction C1 is concentrated by evaporation to ⅙ of the volume under exclusion of oxygen. The resulting suspension is stored in a nitrogen atmosphere for 2 hours at 4° C., the separated product is aspirated off, washed with a little cold methanol and dried at 40° C. and 20 mbars. 0.55 g of tetrahydrofolic acid dimethylester benzene sulphonate is obtained (0.87 mmole, 44% of theoretical yield). The ratio of the diastereomers of the tetrahydrofolic acid dimethylester benzene sulphonate (6S,αS):(6R,αS) is 99:1, determined by means of HPLC. $[a]_{589}=-69.8°$ (c=1 in dimethyl sulphoxide). The substance breaks down above 150° C.

$^1$H-NMR in DMSO-$d_6$: 10.61 (1H, bs), 8.35 (1H, d), 7.6-7.74 (m), 7.51 (1H, bs), 7.30-7.37 (m), 6.70 (2H, d, 2H, bs), 4.42 (2H, m), 3.63 (3H, s), 3.58 (3H, s), 3.50 (1H, m), 3.38 (1H, m), 3.28 (1H, m), 2.44 (2H, m), 2.01-2.13 (2H, m)

b Hydrolysis of The Tetrahydrofolic Acid Dimethylester Benzene Sulphonate:

0.55 g of tetrahydrofolic acid dimethylester benzene sulphonate [(6S,αS):(6R,αS)=99:1] (0.87 mmole) and 0.32 g of sodium carbonate (3.02 mmole) are dissolved in 4 ml of water under exclusion of oxygen. The solution is heated to 85° C. and after 30 minutes the pH is adjusted to 7.5 with 37% hydrochloric acid. 0.2 g of benzene sulphonic acid in 0.6 ml of water is added at 75° C. and then the pH is adjusted to 0.8 with 37% hydrochloric acid. The solution is allowed to cool to room temperature and stirred for a further three hours. The product is filtered off by suction and dried in a drying chamber at 30° C. and 20 mbars for 4 days. 8.4 g of tetrahydrofolic acid benzene sulphonate are obtained (13.92 mmoles, 88% of theoretical yield).

The diastereomer ratio of tetrahydrofolic acid benzene sulphonate (6S,αS):(6R,αS) is 99:1. The method of determination is outlined in EP-0 495 204.

The properties of the tetrahydrofolic acid benzene sulphonate are identical to those of the product described in EP-0 495 204 B1.

The invention claimed is:

1. A process for preparing tetrahydropterin of the following formula

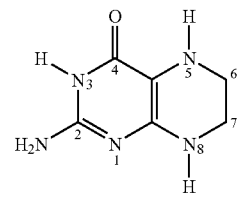

or a tetrahydropterin compound of said tetrahydropterin that is substituted at the 6-, or 7- or 6- and 7-position or positions, comprising hydrogenating pterin of the following formula

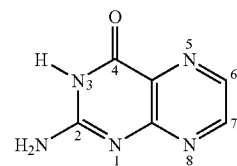

or a pterin compound of said pterin that is monosubstituted at the 6-, or 7- or 6- and 7-position or positions, with hydrogen in a polar reaction medium in the presence of a hydrogenation catalyst that is a metal complex that is soluble in the reaction medium, wherein the catalyst contains a ligand which is (i) triarylphosphine, (ii) tetramethylene phenylphosphine (iii) pentamethylene phenylphosphine, or (iv) a bidentate ligand with a tertiary amine group and a phosphine group or with two tertiary

39 phosphine groups as complexing groups, wherein the bidentate ligands form together with a metal atom a five- to ten membered ring.

2. A process according to claim 1, wherein the polar reaction medium is an aqueous or alcoholic reaction medium.

3. A process according to claim 1, wherein the pterin compound is folic acid, a folic acid salt, a folic acid ester, a folic acid ester salt or a dihydro form thereof, with the proviso that in the event of using folic acid, a carboxylic acid thereof or a dihydro form thereof, the reaction medium is aqueous, and in the event of using a folic acid ester, a folic acid ester salt or a dihydro form thereof, the reaction medium is an alcohol.

4. A process according to claim 1, wherein the metal complex contains a chiral ligand.

5. A process according to claim 3, wherein the metal complex contains a chiral ligand.

6. A process according to claim 5, wherein the folic acid ester salt is of formula III and is in the form of a single enantiomer or a mixture of enantiomers of formula III,

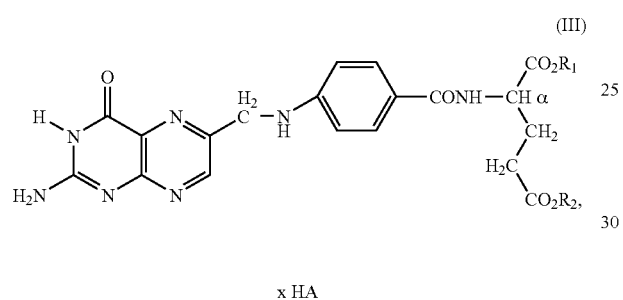

x HA in which
one of $R_1$ or $R_2$ is H, and the other one of $R_1$ or $R_2$ is a monovalent hydrocarbon radical or a hydrocarbon radical attached via a carbon atom in which one or more carbon atoms are each independently replaced by oxygen, sulfur, NH, —N=, or —N($C_1$-$C_4$ Alkyl)-, or
both $R_1$ and $R_2$ independently of one another represent a monovalent hydrocarbon radical or a hydrocarbon radical attached via a carbon atom in which one or more carbon atoms are each independently replaced by oxygen, sulfur, NH, —N=, or —N($C_1$-$C_4$ Alkyl)-,
HA stands for a monobasic to tribasic inorganic or organic acid, and
x denotes an integer from 1 to 6 or a fractional number between 0 and 6.

7. A process according to claim 6, wherein HA is unsubstituted or substituted phenylsulphonic acid.

8. A process according to claim 1, wherein said process is carried out at a hydrogen pressure of 1 to 500 bars.

9. A process according to claim 1, wherein said process is carried out at a temperature is 0 to 150° C.

10. A process according to claim 1, wherein the molar ratio of pterin or pterin compound to catalyst is 10 to 100,000.

11. A process according to claim 1, wherein the reaction medium is water or water in admixture with an organic solvent.

12. A process according to claim 2, wherein the alcoholic reaction medium is an alcohol, or an alcohol in admixture with an organic solvent.

13. A process according to claim 1, wherein the metal complex contains a d-8 metal.

40

14. A process for preparing tetrahydropterin of the following formula

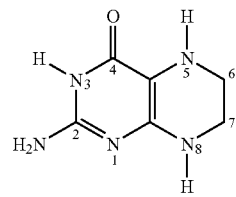

or a tetrahydropterin compound of said tetrahydropterin that is substituted at the 6-, or 7- or 6- and 7-position or positions,
comprising hydrogenating pterin of the following formula

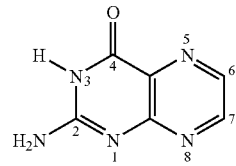

or a pterin compound of said pterin that is monosubstituted at the 6-, or 7- or 6- and 7-position or positions,
with hydrogen in alcohol or in alcohol in admixture with an organic solvent in the presence of a hydrogenation catalyst that is a metal complex that is soluble in the reaction medium.

15. A process according to claim 3, wherein the hydrogenation is carried out at elevated pressure.

16. A process according to claim 1, wherein the metal complex contains iridium, rhodium or ruthenium.

17. A process for preparing tetrahydropterin of the following formula

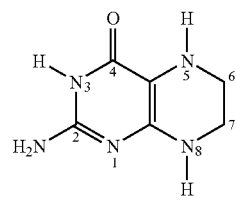

or a tetrahydropterin compound of said tetrahydropterin that is substituted at the 6-, or 7- or 6- and 7-position or positions,
comprising hydrogenating pterin of the following formula

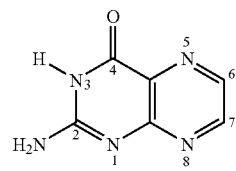

or a pterin compound of said pterin that is monosubstituted at the 6-, or 7- or 6- and 7-position or positions, with hydrogen in alcohol or in alcohol in admixture with an organic solvent in the presence of a hydrogenation catalyst that is a metal complex that is soluble in the reaction medium, wherein the pterin compound is folic acid, a folic acid salt, a folic acid ester, a folic acid ester salt or a dihydro form thereof, with the proviso that in the event of using folic acid, a carboxylic acid thereof or a dihydro form thereof, the reaction medium is aqueous, and in the event of using a folic acid ester, a folic acid ester salt or a dihydro form thereof, the reaction medium is an alcohol.

18. A process according to claim 1, wherein the pterin compound is a pterin that is substituted in the 6-position.

19. A process according to claim 1, wherein the pterin compound is of formula (A)

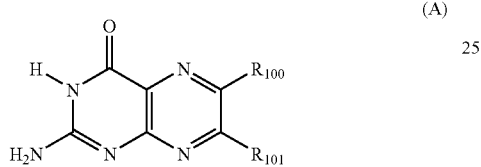

(A)

in which $R_{101}$ is H or independently has the meaning of $R_{100}$, and $R_{100}$ is an organic radical attached via a C, O or N atom and having 1 to 50 carbon atoms.

20. A process according to claim 19, wherein $R_{100}$ contains 1 to 30 carbon atoms and is not interrupted or is interrupted by one or more of —O—, —NH—, —N($C_1$-$C_4$-alkyl)-, —C(O)—, —C(O)O—, —OC(O)—, —OC(O)O—, —C(O)NH—, —NHC(O)—, —NHC(O)O—, —OC(O)NH—, —NHC(O)NH—, —C(O)N($C_1$-$C_4$-alkyl)-, —N($C_1$-$C_4$-alkyl)C(O)—, —N($C_1$-$C_4$-alkyl)C(O)O—, —OC(O)N($C_1$-$C_4$-alkyl)-, —N($C_1$-$C_4$-alkyl)C(O)N($C_1$-$C_4$-alkyl)-, and which is unsubstituted or is substituted with F, Cl, Br, —CN, —OCN, —NCO, —OH, —NH$_2$, —NH$C_1$-$C_4$-alkyl, —N($C_1$-$C_4$-alkyl)$_2$, $C_1$-$C_4$-alkyl, $C_1$-$C_4$-haloalkyl, $C_1$-$C_4$-hydroxyalkyl, $C_1$-$C_4$-alkoxy, $C_1$-$C_4$-haloalkoxy, —C(O)OH, —C(O)O$M_{100}$, —C(O)O$C_1$-$C_4$-alkyl, —C(O)NH$_2$, —C(O)NH$C_1$-$C_4$-alkyl, —C(O)N($C_1$-$C_4$-alkyl)$_2$, $R_{102}$—C(O)O—, $R_{102}$—OC(O)O—, $R_{102}$—C(O)NH—, $R_{102}$—C(O)N($C_1$-$C_4$-alkyl)-, $R_{102}$—NHC(O)NH—, $R_{103}$C(O)— or —CH(O), wherein $M_{100}$ is Li, K, Na, $NH_4^+$, or ammonium with 1 to 16 carbon atoms, $R_{102}$ is $C_1$-$C_8$-alkyl, $C_5$- or $C_6$-cycloalkyl, phenyl or benzyl, and $R_{103}$ is $C_1$-$C_4$-alkyl, phenyl or benzyl.

21. A process for preparing tetrahydropterin of the following formula

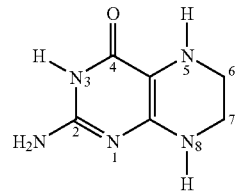

or a tetrahydropterin compound of said tetrahydropterin that is substituted at the 6-, or 7- or 6- and 7-position or positions, comprising hydrogenating pterin of the following formula

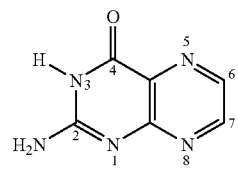

or a pterin compound of said pterin that is monosubstituted at the 6-, or 7- or 6- and 7-position or positions, with hydrogen in a polar reaction medium in the presence of a hydrogenation catalyst that is a metal complex that is soluble in the reaction medium of formula XLIV, XLIVa or XLIVb, $[X_7Me_2YZ]$ (XLIV), $[X_7Me_2Y]^+A_2^-$ (XLIVa)

$[X_7Ru(II)X_8X_9]$ (XLIVb), in which

Y stands for monoolefin ligands or a diene ligand;

$X_7$ represents an achiral or chiral ditertiary diphosphine, that forms a 5 to 7 membered ring with the metal atom $Me_2$ or Ru;

$X_7$ represents an achiral or chiral ligand that forms a 5 to 7 membered ring with the metal atom $Me_2$ or Ru, wherein said ligand contains two tertiary phosphine groups;

$Me_2$ denotes Ir(I) or Rh(I);

Z represents —Cl, —Br, or —I; and $A_2$ is $ClO_4^-$, $CF_3^-SO_3^-$, $CH_3SO_3^-$, $HSO_4^-$, $BF_4^-$, B(Phenyl)$_4^-$, $PF_6^-$, $SbCl_6^-$, $AsF_6^-$ or $SbF_6^-$;

$X_8$ and $X_9$ are the same or different and have the meaning of Z or $A_2$, or $X_8$ has the meaning of Z or $A_2$ and $X_9$ stands for hydride.

22. A process according to claim 6, wherein $R_1$ and/or $R_2$ are, each independently, pyrrolidinyl, piperidinyl, morpholinyl, tetrahydropyranyl, piperazinyl, pyrrolidinyl methyl, pyrrolidinyl ethyl, piperidinyl methyl, piperidinyl ethyl, morpholinyl methyl, morpholinyl ethyl, tetrahydropyranyl methyl, tetrahydropyranyl ethyl, piperazinyl methyl or piperazinyl ethyl.

* * * * *